(12) United States Patent
Schneider et al.

(10) Patent No.: US 11,468,984 B2
(45) Date of Patent: Oct. 11, 2022

(54) DEVICE, METHOD AND APPLICATION FOR ESTABLISHING A CURRENT LOAD LEVEL

(71) Applicant: SOMA ANALYTICS UG (HAFTUNGSBESCHRÄNKT), Munich (DE)

(72) Inventors: Peter Schneider, Dresden (DE); Johann Huber, Bruckmühl (DE); Christopher Lorenz, Munich (DE); Diego Alberto Martin-Serrano Fernandez, London (GB)

(73) Assignee: SOMA ANALYTICS UG (HAFTUNGSBESCHRÄNKT), Munich (DE)

( * ) Notice: Subject to any disclaimer, the term of this patent is extended or adjusted under 35 U.S.C. 154(b) by 0 days.

(21) Appl. No.: 16/850,984

(22) Filed: Apr. 16, 2020

(65) Prior Publication Data
US 2020/0237302 A1 Jul. 30, 2020

Related U.S. Application Data

(63) Continuation of application No. 14/418,374, filed as application No. PCT/EP2013/066241 on Aug. 1, 2013, now abandoned.

(30) Foreign Application Priority Data

Aug. 1, 2012 (DE) .................... 10 2012 213 618.5
Aug. 17, 2012 (DE) .................... 10 2012 214 697.0

(51) Int. Cl.
*A61B 5/00* (2006.01)
*G16H 40/67* (2018.01)
(Continued)

(52) U.S. Cl.
CPC ............ *G16H 40/67* (2018.01); *A61B 5/165* (2013.01); *A61B 5/4803* (2013.01);
(Continued)

(58) Field of Classification Search
CPC ........ G16H 40/67; G16H 50/20; G10L 25/66; G10L 25/63; A61B 5/165; A61B 5/4809;
(Continued)

(56) References Cited

U.S. PATENT DOCUMENTS 5,745,034 A 4/1998 Andersen et al.
6,129,681 A 10/2000 Kuroda et al.
(Continued)

FOREIGN PATENT DOCUMENTS

DE 10 2009 043 775 A1 4/2011
EP 2 014 225 A2 1/2009
(Continued)

OTHER PUBLICATIONS

International Search Report in PCT application PCT/EP2013/066241 dated Dec. 9, 2013.
(Continued)

*Primary Examiner* — Rex R Holmes
(74) *Attorney, Agent, or Firm* — Maschoff Brennan

(57) ABSTRACT

The invention relates to a device, a method, a computer program product and an application for establishing a current load level of a user. The device and the method comprise a mobile terminal, which comprises at least one sensor generating signal data and a plurality of available applications for use by the user and also an evaluation unit. According to the invention, provision is made for the mobile terminal to comprise an application, which is configured as further application and establishes a plurality of biometric data in respect of the user, at least from the signal data or from available applications used by the user, and to make
(Continued)

said data available to the evaluation unit, and for the evaluation unit to determine the current load level of the user from the biometric data.

18 Claims, 13 Drawing Sheets

(51) Int. Cl.
| | |
|---|---|
| G10L 25/66 | (2013.01) |
| A61B 5/16 | (2006.01) |
| G10L 25/63 | (2013.01) |
| G06N 3/04 | (2006.01) |
| G16H 50/20 | (2018.01) |
| G06N 3/08 | (2006.01) |
| G16B 40/20 | (2019.01) |
| A61B 5/11 | (2006.01) |
| G16B 40/00 | (2019.01) |

(52) U.S. Cl.
CPC .......... *A61B 5/4809* (2013.01); *A61B 5/4812* (2013.01); *A61B 5/4815* (2013.01); *A61B 5/4884* (2013.01); *A61B 5/7267* (2013.01); *G06N 3/04* (2013.01); *G06N 3/0454* (2013.01); *G06N 3/084* (2013.01); *G06N 3/088* (2013.01); *G10L 25/63* (2013.01); *G10L 25/66* (2013.01); *G16B 40/20* (2019.02); *G16H 50/20* (2018.01); *A61B 5/1124* (2013.01); *A61B 5/486* (2013.01); *A61B 5/4806* (2013.01); *A61B 5/6898* (2013.01); *A61B 5/7264* (2013.01); *G06N 3/0445* (2013.01); *G16B 40/00* (2019.02)

(58) Field of Classification Search
CPC ... A61B 5/4812; A61B 5/4815; A61B 5/4884; A61B 5/7267; A61B 5/4803; A61B 5/486; A61B 5/1124; A61B 5/6898; A61B 5/7264; A61B 5/4806; G06N 3/0454; G06N 3/084; G06N 3/04; G06N 3/088; G06N 3/0445; G16B 40/00
See application file for complete search history.

(56) References Cited

U.S. PATENT DOCUMENTS

| | | | |
|---|---|---|---|
| 7,613,663 | B1 | 11/2009 | Commons et al. |
| 7,720,696 | B1 | 5/2010 | Berger et al. |
| 2003/0153817 | A1 | 8/2003 | Knagenhjelm |
| 2004/0176991 | A1 | 9/2004 | McKennan et al. |
| 2005/0245790 | A1 | 11/2005 | Bergfalk et al. |
| 2006/0224051 | A1 | 10/2006 | Teller et al. |
| 2008/0208016 | A1 | 8/2008 | Hughes et al. |
| 2008/0281220 | A1 | 11/2008 | Sharifpour |
| 2009/0254369 | A1* | 10/2009 | Mohaideen ............ G16H 15/00 705/3 |
| 2009/0326981 | A1 | 12/2009 | Karkanias et al. |
| 2010/0041965 | A1 | 2/2010 | Kang et al. |
| 2010/0123588 | A1 | 5/2010 | Cruz Hernandez |
| 2010/0131028 | A1 | 5/2010 | Hsu et al. |
| 2010/0249624 | A1 | 9/2010 | Peng |
| 2010/0324427 | A1 | 12/2010 | Devot et al. |
| 2011/0015495 | A1 | 1/2011 | Dothie et al. |
| 2011/0022332 | A1 | 1/2011 | Kailas et al. |
| 2011/0022392 | A1 | 1/2011 | Iwamoto |
| 2011/0124977 | A1 | 5/2011 | Winarski |
| 2011/0218950 | A1* | 9/2011 | Mirowski .......... G06K 9/00536 706/12 |
| 2011/0224510 | A1 | 9/2011 | Oakhill |
| 2011/0283190 | A1 | 11/2011 | Poltorak |
| 2011/0306850 | A1 | 12/2011 | Hatlestad et al. |
| 2012/0036016 | A1* | 2/2012 | Hoffberg .......... H04N 21/42201 705/14.58 |
| 2012/0116186 | A1 | 5/2012 | Shrivastav et al. |
| 2012/0116187 | A1 | 5/2012 | Hayes et al. |
| 2012/0197622 | A1 | 8/2012 | Jain |
| 2012/0289789 | A1* | 11/2012 | Jain ..................... A61B 5/0022 600/301 |
| 2013/0262096 | A1 | 10/2013 | Wilhelms-Tricarico et al. |

FOREIGN PATENT DOCUMENTS

| | | |
|---|---|---|
| WO | 2008/019040 A2 | 2/2008 |
| WO | 2010/136786 A2 | 12/2010 |
| WO | 2012/008961 A1 | 1/2012 |
| WO | 2012/085687 A2 | 6/2012 |

OTHER PUBLICATIONS

Written Opinion in PCT application PCT/EP2013/066241 dated Dec. 9, 2013.
http://healthreviser.com/content/stress-monitor, accessed Jan. 29, 2015.
http://www.whatsmym3.com/, accessed Jan. 29, 2015.
Bethge, P., "Tech Pioneers Track Bodily Functions Day and Night", Accessed at:http://www.spiegel.de/international/world/new-trend-towards-self-monitoring-using-high-techequipment-a-829454.html, accessed on Mar. 13, 2015, 3 pages.
Kriesel, D., "A Brief Introduction to Neural Networks", Accessed at http://www.dkriesel.com/_media/science/neuronalenetze-en-zeta2-2col-dkrieselcom.pdf, 2005, 244 pages.
Georgiev et al., Low-resource Multi-task Audio Sensing for Mobile and Embedded Devices via Shared Deep Neural Network Representations, Mar. 2010, Proceedings of the ACM on Interactive, Mobile, Wearable and Ubiquitous Technologies, vol. 9, No. 4, Article 39:1-19.

* cited by examiner

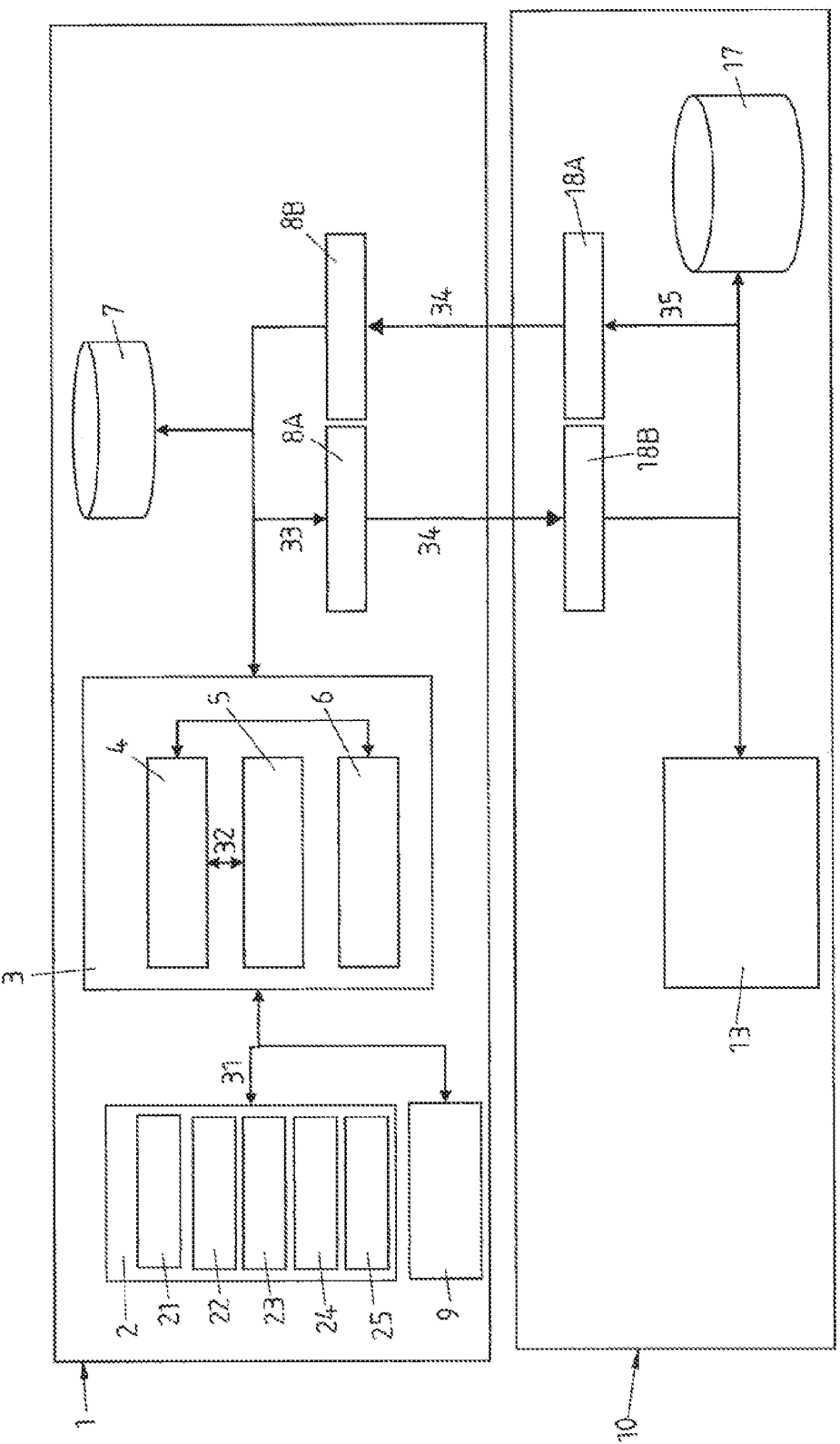

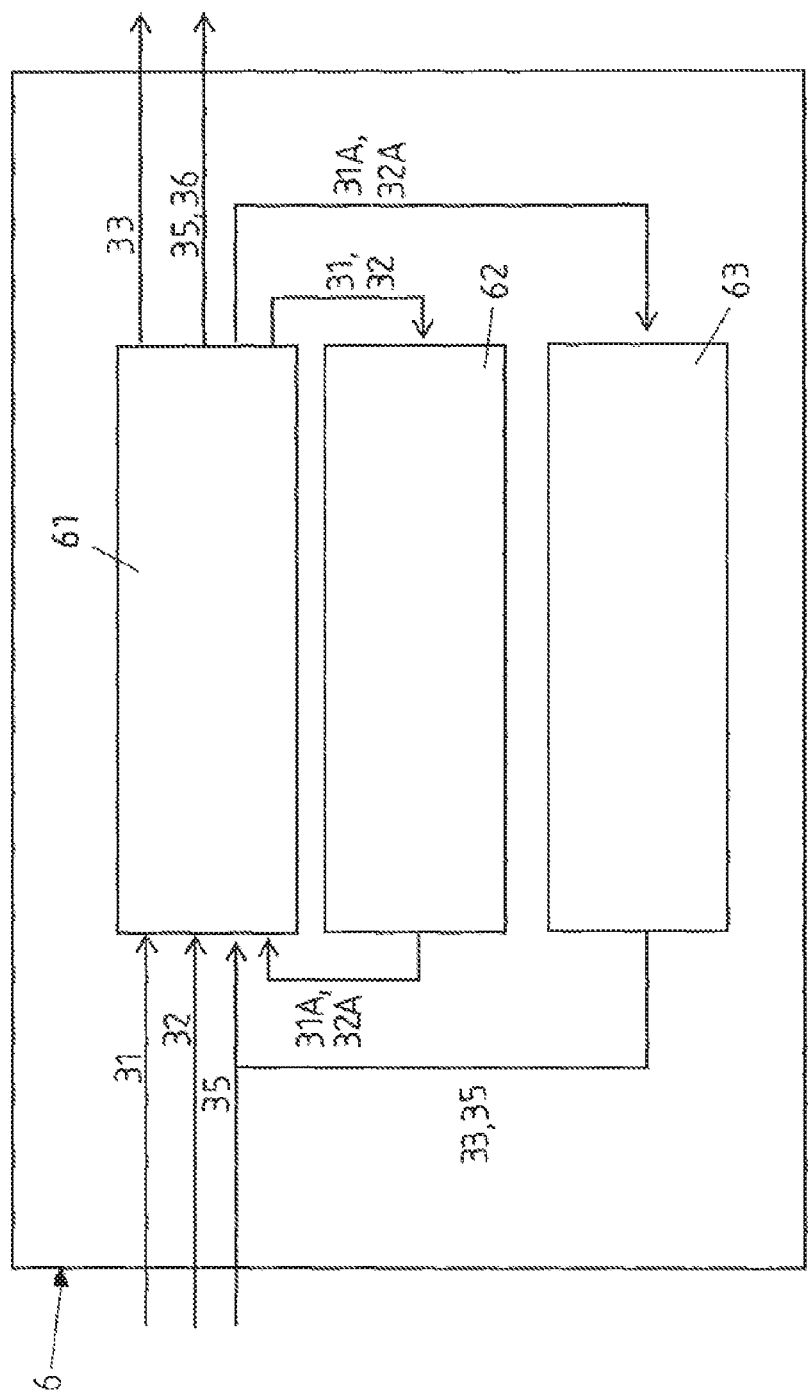

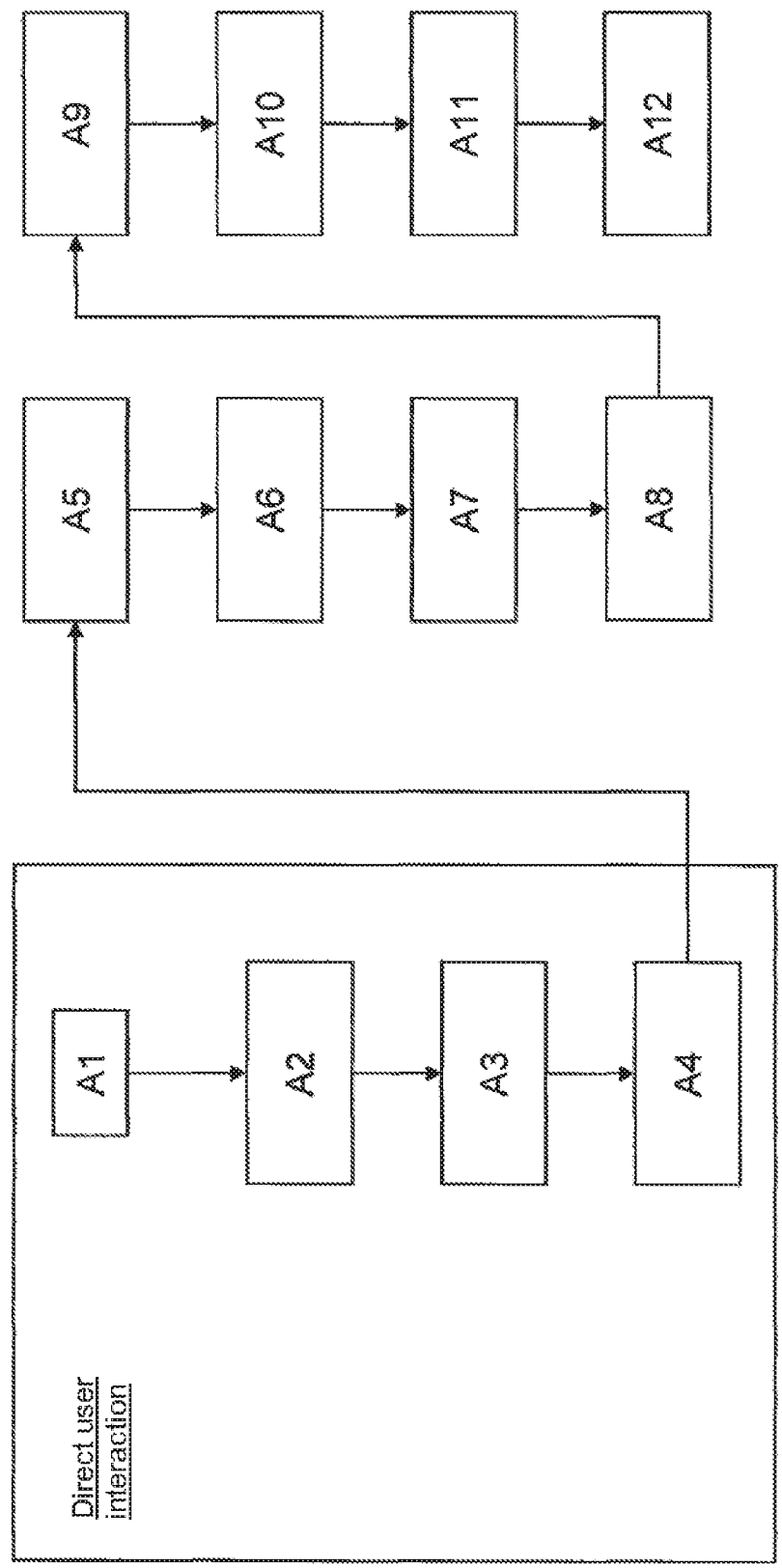

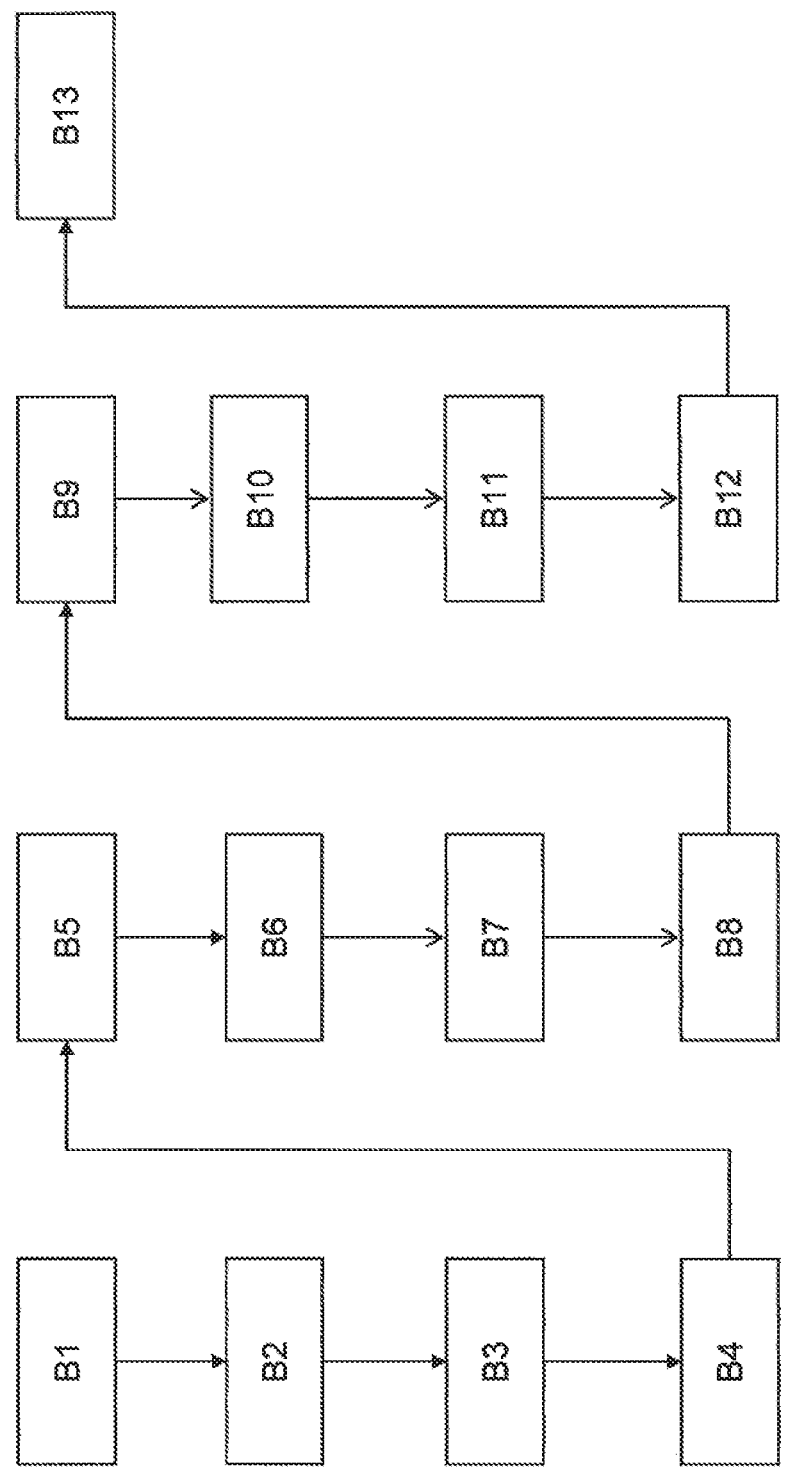

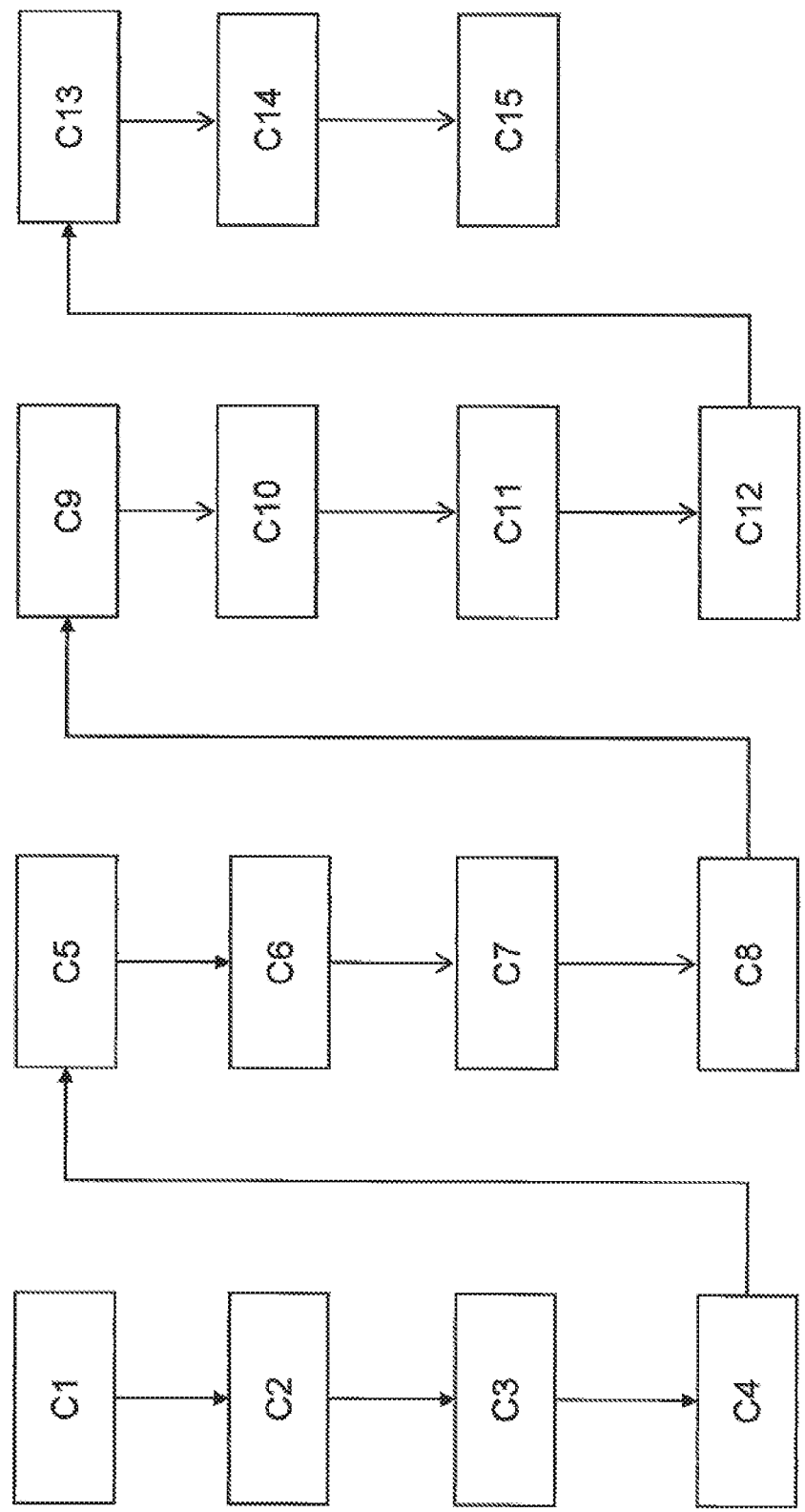

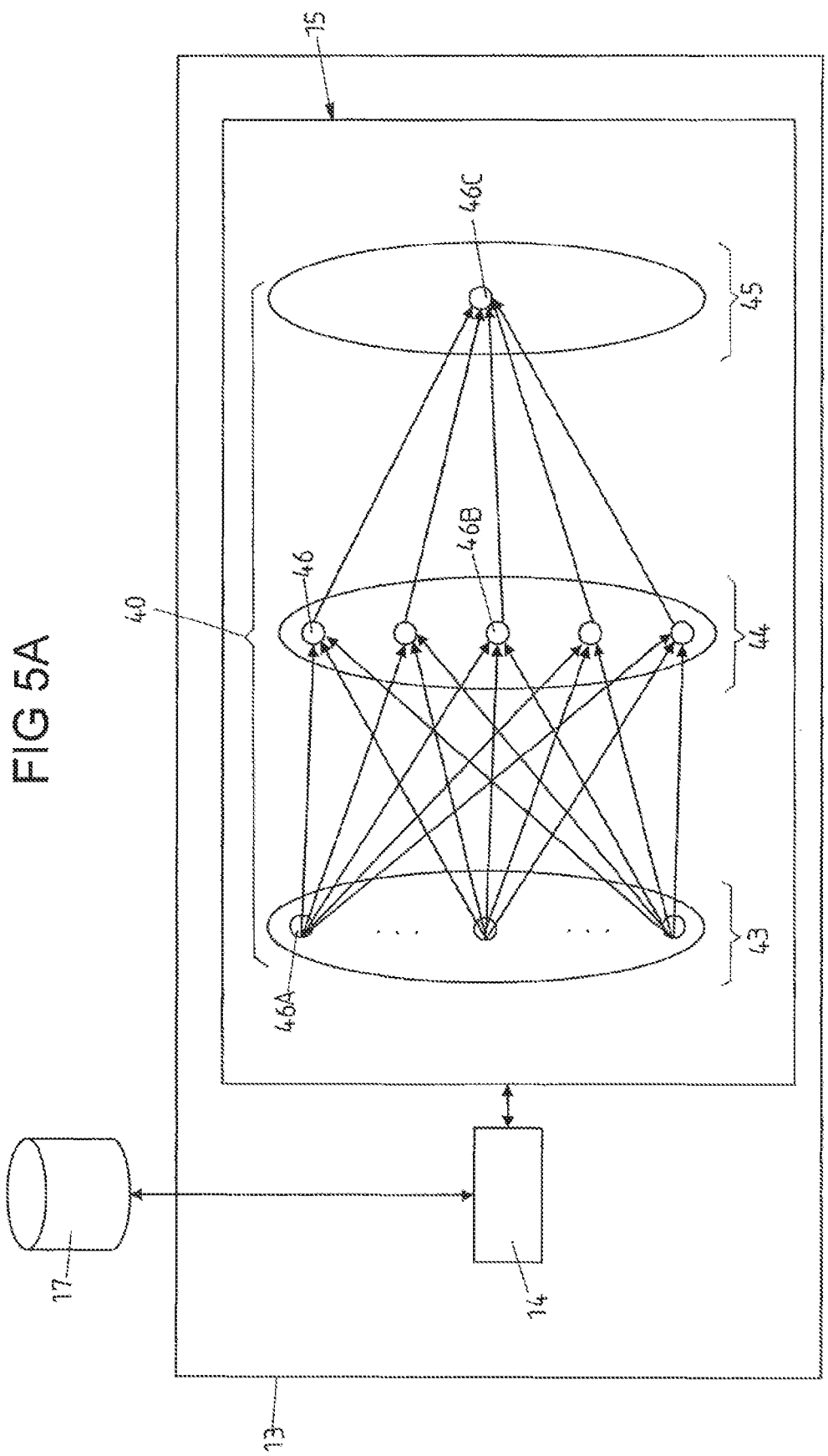

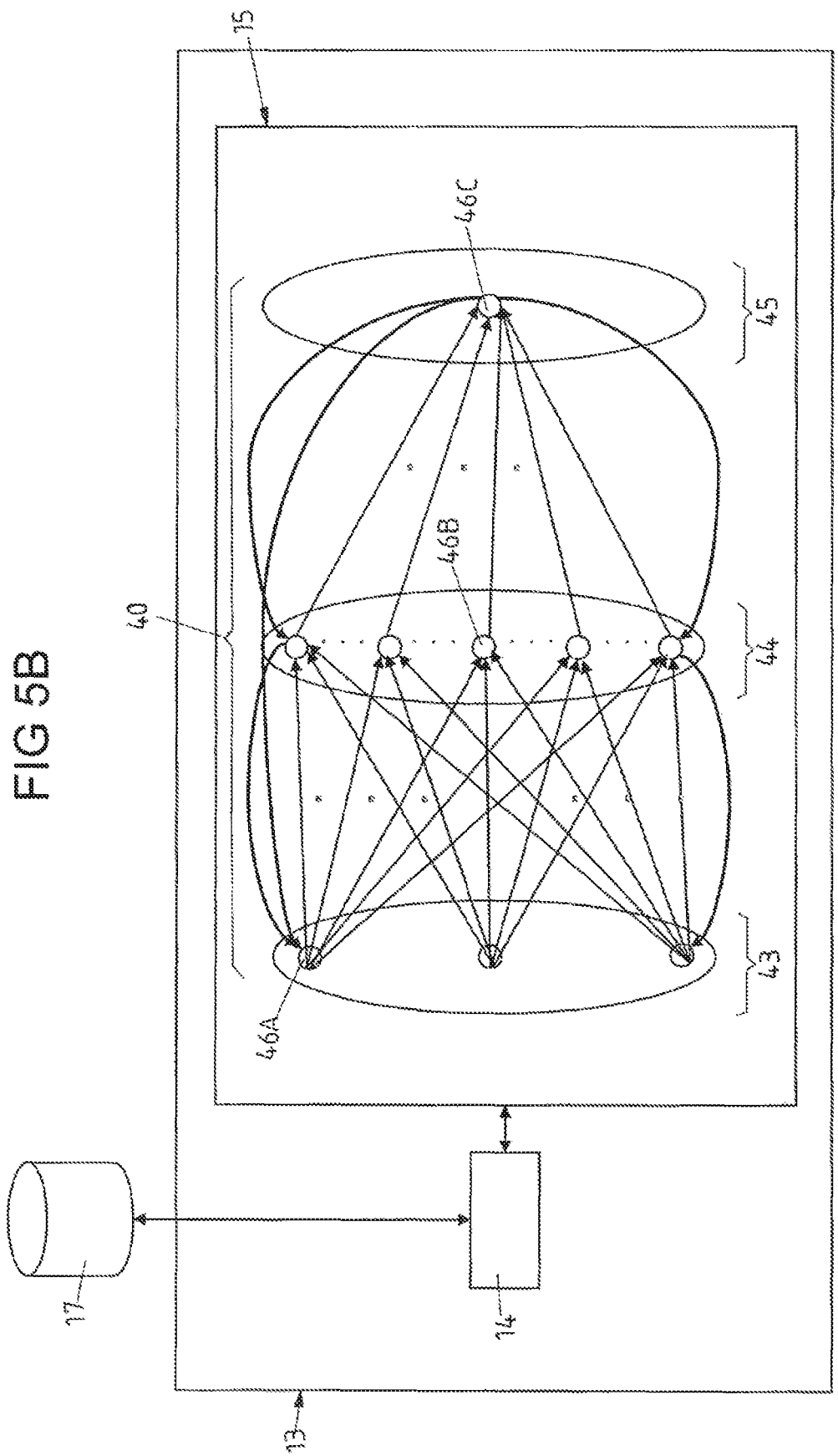

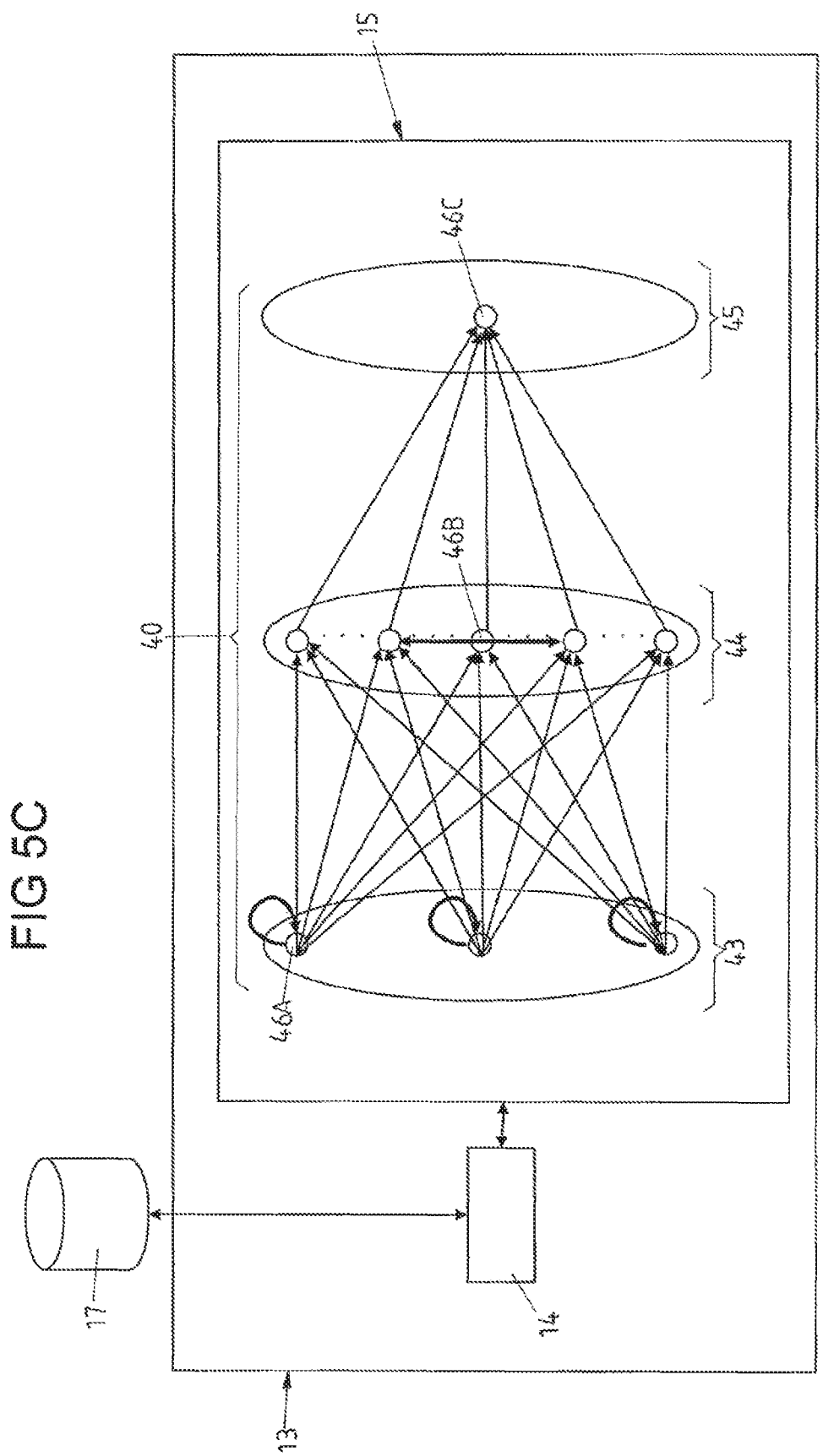

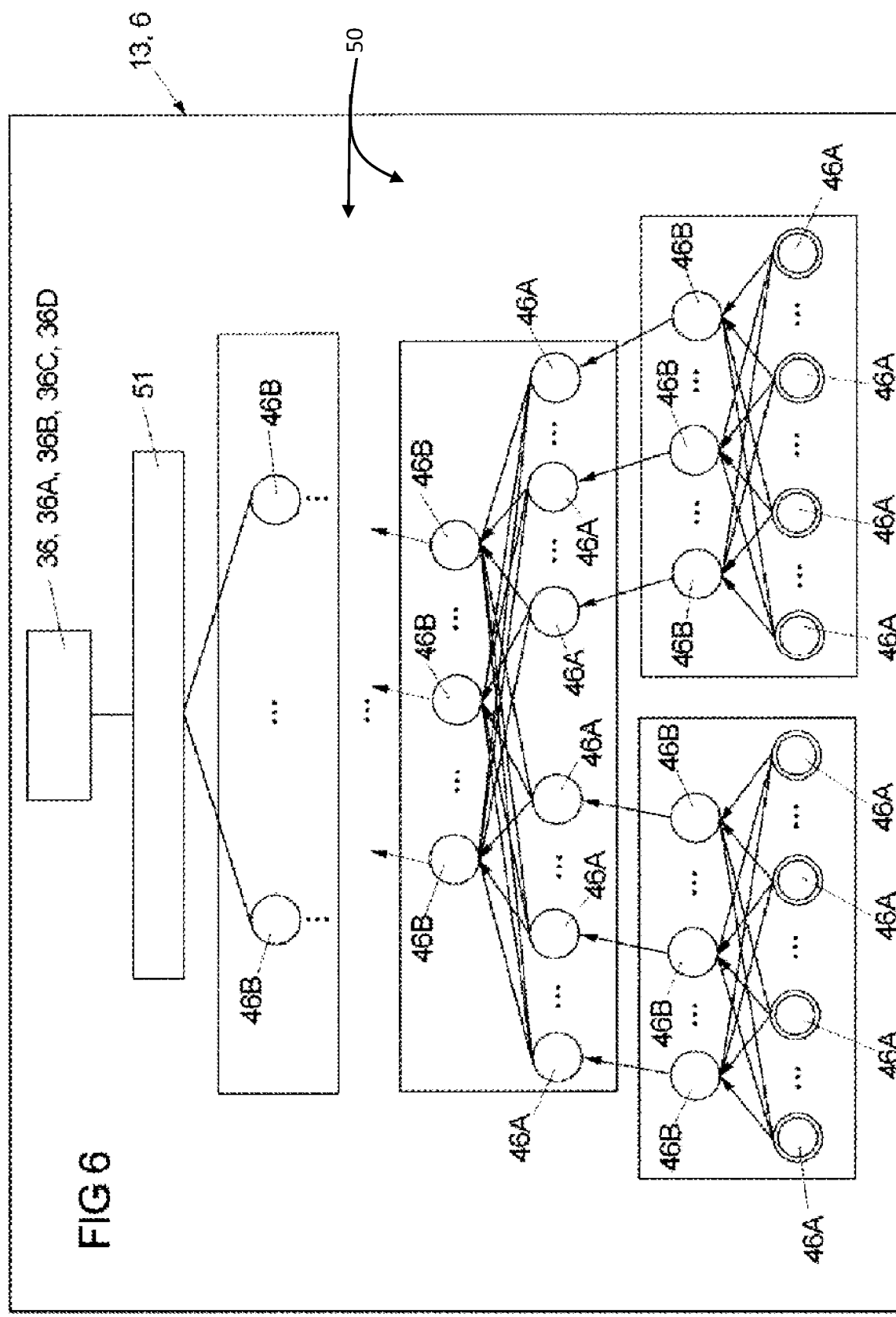

DEVICE, METHOD AND APPLICATION FOR ESTABLISHING A CURRENT LOAD LEVEL

CROSS-REFERENCE TO RELATED APPLICATIONS

This application claims priority to German Patent Application No. DE102012213618, filed on Aug. 1, 2012. The foregoing patent application is herein incorporated by reference.

The present invention relates to an apparatus for ascertaining a current stress level for a user according to the preamble of claim 1, to a method for ascertaining a current stress level, to a computer program product and to an application for a mobile terminal.

PRIOR ART

According to the preamble of claim 1, a mobile terminal is provided that has at least one sensor integrated in the mobile terminal for producing signal data and has a plurality of available applications for use by the user. In addition, an evaluation unit is provided. The evaluation unit is provided particularly to evaluate signal data.

By way of example, the mobile terminal according to the preamble is a smartphone such as an iPhone or another smartphone, which is equipped with an operating system, such as an iOS or Android operating system for a mobile terminal, and has an integrated sensor, for example a GPS sensor for ascertaining the current position. The mobile terminal has a plurality of standard applications installed on it, such as a telephony application for setting up and conducting a telephone call via a mobile radio link and/or an application for writing, sending and receiving SMSs and/or a browser application for accessing web pages on the Internet. In addition, the operating system allows the installation and execution of further applications, which can be downloaded from an online shop for mobile applications on the Internet, for example. The further application can request and process data pertaining to the current location of the mobile terminal from the GPS sensor, for example, and can transmit said data to a central server via the mobile radio network, for example via a GPRS or UMTS connection. Such tracking data can be stored on the server and evaluated in an evaluation unit arranged in the central server, for example in order to provide the user with location-based services, such as a locating service for tracking the whereabouts of a child for his parents, what is known as a Childtracker. Location-based services are currently widely advertized on the market and in great demand, as a result of which smartphones have now become prevalent, particularly in younger demographic groups.

In addition, there are differently designed apparatuses and methods that use special devices for sensor-based measurement of specific vital functions and determine a current stress level from the measured values. By way of example, the Stress Monitor (see http://www.healthrevisercom/content/stress-monitor) thus uses a clip worn on the ear of the user to ascertain the heart rate of the user and uses this singular indicator to determine a current stress level.

Further methods known to date determine a current stress level for a person on the basis of questionnaires, for example. Such a method is provided by My Mood Monitor (see http://www.whatsmym3.com), for example, on the basis of an online questionnaire. When performed repeatedly, such methods based on questionnaire data can help to show the alteration in a stress level over time. In particular, they can provide people affected by depression and/or stress with a tool for monitoring the success of measures taken in order to improve stress level.

The cited apparatuses and methods for ascertaining a current stress level have the disadvantage that the current stress level is determined on the basis of very few biometric data (for example subjective questionnaire data or objective sensor data that measure a vital function), which means that different categories of biometric data are not combined. Therefore, the current stress level can be determined less reliably than when a large number of different categories of biometric data are used.

Furthermore, the aforementioned sensor-based apparatuses resort to special devices designed precisely for this instance of application, which are equipped with integrated sensors that capture a specific category of biometric data, such as the heart rate or the body temperature or another vital function. These devices need to be worn by the user on his body, for example, in order to determine his current stress level. This firstly means increased outlay in terms of hardware and cost, since measuring a vital function requires a dedicated device with a sensor for measuring precisely this vital function. Furthermore, fitting and wearing a special apparatus with an integrated sensor on or in direct proximity to the body is a nuisance for the wearer, particularly a restriction of comfort and wellbeing.

By contrast, the aforementioned questionnaire-based methods require a high level of additional effort from the user. By way of example, the user thus needs to regularly answer questionnaire data, for example using a computer via the Internet, and then autonomously manage, compare and rate the results that vary over time.

STATEMENT OF PROBLEM

It is therefore an object of the present invention to provide an apparatus and also a method and an application of the type cited at the outset that overcome the aforementioned disadvantages. In particular, it is an object of the invention to provide an apparatus and a method, a computer program product and also an application that determine a current stress level for a user with a high level of reliability, with the additional outlay for the user in terms of cost and time being minimized without restricting the comfort of the user, since the invention dispenses with the use of additional devices and/or sensors that need to be worn on or close to the body.

The invention achieves this object by means of the features found in the patent claims. Advantageous refinements of the invention can be found in the claims and in the description below.

The present invention comprises a further application that can be installed on a mobile terminal and that ascertains a multiplicity of biometric data from a user. In order to ascertain the biometric data, the further application interacts with other components that are likewise arranged in the mobile terminal. By way of example, the other components are sensors integrated in the mobile terminal and also available applications. An available application denotes an application that is available on a mobile terminal. That is to say an application that is installed and executable on the mobile terminal, such as telephony, SMS, MMS, chat applications and/or browser applications for accessing the Internet and also other applications that are suitable for extracting tactile, acoustic and/or visual biometric features of the user.

By way of example, the mobile terminal is a smartphone or a tablet computer or a PDA or another mobile terminal that the user can use for many diverse purposes, for example for communication.

The mobile terminal has means for installing and executing a further application. By way of example the further application can be obtained via the Internet via an online shop integrated in the operating system of the mobile terminal, such as the App store, or another online shop that supplies compatible applications for the mobile terminal, and can be installed on the mobile terminal directly. The further application may be available in various versions, for example in an iOS version for installation and execution on an iPhone or an iPad and in an Android version for installation and execution on a mobile terminal that supports said Android operating system, or in a further version that is compatible with a further mobile operating system. Alternatively, the further application may be installed, and can be executed, on an interchangeable component of the mobile terminal. By way of example, it may be stored as a SIM application in a memory area on a SIM card that can be operated in the mobile terminal, and can be executed by a separate execution unit integrated on the SIM card.

As a result of a further application according to the invention, in a version compatible with the mobile terminal, being installed and executed on a mobile terminal of the type described at the outset, the portion of the apparatus for ascertaining a current stress level that is arranged on the mobile terminal is obtained.

The further application ascertains the biometric data firstly from signal data that are produced by sensors integrated in the mobile terminal, and secondly biometric data are extracted from the use data of other applications installed on the mobile terminal.

Determination of a plurality of biometric data is firstly facilitated by virtue of mobile terminals, such as smartphones, being equipped with an increasing number of sensors as standard. Furthermore, determination of further biometric data is also facilitated by virtue of users increasingly satisfying their interaction and communication needs by using such devices, and hence biometric data pertaining to the categories speech and social interaction, for example, being able to be derived from use data pertaining to communication applications of the mobile terminal directly, and without additional effort and restriction of comfort for the user.

By way of example, the further application can use voice analysis to ascertain biometric data pertaining to speech, such as volume, speech rate and/or modulation capability, from the use data from a telephony application installed on the mobile terminal, particularly from the voice data from the user that are ascertained via the microphone of the mobile handset and that are transmitted from the mobile terminal to the communication partner via a radio network, for example. Alternatively, the voice data from the user can come from using other available applications, for example from applications that are controlled by the user using voice control.

From the use data from an SMS application installed on the mobile terminal, the further application can determine the number of SMS messages sent and received and the number of different receivers and senders of SMS messages, and hence can determine biometric data pertaining to social interaction.

By way of example, a sensor integrated in the mobile terminal may be a gyroscope or gyroscopic instrument. A gyroscope is used for position finding in space and is increasingly widespread in smartphones currently advertized on the market, such as in the iPhone 4. The gyroscope and further sensors that are integrated in the mobile terminal, such as an acceleration sensor and/or a light sensor, can be used to ascertain biometric data pertaining to the sleep structure of the user. To this end, the mobile terminal is positioned on the mattress at night and the movements of the user during the night are detected by the sensors. The further application collects the signal data produced by gyroscope, acceleration sensor and/or light sensor and ascertains biometric data therefrom pertaining to sleep quality and sleep profile, such as time of sleep onset, sleep duration and/or sleep stages.

In addition, it is also possible for questionnaire data answered by the user, which questionnaire data are requested using a web form in a browser application or in a form that provides the further application, to be part of the biometric data ascertained by the further application. Since answering questionnaire data generates additional effort for the user, these data showing the subjective stress level should be requested only once or as rarely as possible.

In one possible embodiment, the biometric data are ascertained constantly by the further application while the mobile terminal is in operation. The mobile terminal is configured such that the further application is started automatically, for example, when the mobile terminal is switched on and is operated continually in the background until the mobile terminal is switched off, without the need for further interaction with the user. Similarly, the mobile terminal can be configured such that the user can activate, configure and deactivate the further application autonomously and in this way controls the times at which biometric user data are meant to be tracked by the further application and provided for evaluation.

Once the further application has been activated, the signal data produced by the sensors integrated in the mobile terminal, which signal data are tracked by the further application, are constantly received by the further application and the biometric data are ascertained therefrom. Similarly, use data from standard applications used by the user, which are tracked by the further application, such as telephony and/or SMS applications, are constantly evaluated by the further application and biometric data are determined therefrom.

The biometric data determined by the further application can be divided into different categories. The biometric data ascertained from the further application belong to the categories sleep, speech, motor functions, social interaction, economic data, personal data and questionnaire data.

The biometric data ascertained by the further application can be evaluated by a first evaluation apparatus, which is provided in the further application, on the mobile terminal. The biometric data ascertained by the further application can alternatively be evaluated by a second evaluation apparatus on a central server. The second evaluation apparatus can increase the quality of the evaluation further.

The biometric data ascertained by the further application are transmitted from the mobile terminal to a central server using standard means that the mobile terminal provides. The transmission of the biometric data is effected in pseudonymized form. To this end, the user is managed on the central server under a pseudonym, rather than under his real name or another identifier identifying the user. The transmitted biometric data are associated with the user by means of the pseudonym. In order to increase security further, the biometric data are transmitted in encrypted form.

For transmission, the data to be transmitted are transferred from the further application to a transmission unit arranged on the mobile terminal. The transmission unit is responsible for setting up, maintaining and clearing down a connection to a network, for example a GPRS or UMTS connection to a mobile radio network to which the data are transmitted. Transmission is effected only when the mobile terminal is in transmission mode. The transmission unit can also be designed for transmission via different networks, for example one or more mobile radio network(s) and/or a wireless connection to a local area network, for example based on an IEEE-802 Standard, such as a WLAN or a WPAN connection. A transmission network, for example a mobile radio network, and possibly further networks connected to said transmission network via gateways, for example, such as the Internet, via which gateways the central server can be reached, is used to transmit the data to the central server.

In addition, there is the possibility of the data ascertained by the further application first of all being stored on a local memory unit arranged on the mobile terminal before the data are transmitted to the central server. This is necessary particularly when the transmission unit is temporarily incapable of transmitting the data via a transmission network. By way of example, when there is no connection to a transmission network, for example when the mobile terminal is in flight mode and hence the transmission unit is deactivated or when the transmission unit cannot set up a connection to a transmission network because the mobile terminal is outside the transmission range of a transmission network.

The biometric data can also be analyzed and evaluated by the further application on the mobile terminal directly. In this embodiment, the further application autonomously ascertains a current stress level for the user from the biometric data.

The central server has a reception unit that can be used to receive data from the network, for example from the Internet. When the biometric data from the user are transmitted from the mobile terminal to the central server, the reception unit receives said data and stores them in a central memory unit.

The stored data are transmitted to an evaluation unit arranged on the central server and are analyzed and evaluated by the evaluation unit. The transmitted and stored data comprise a plurality of biometric data pertaining to a user that are used by the evaluation unit in order to ascertain a current stress level for the user.

Since the current stress level is an individual variable and does not involve a comparison with objective standard values, for example, the method disposed in this application is not a diagnostic method. Instead, it is a method that ascertains, collects and analyzes biometric data pertaining to a user and provides the user with the results of the analysis in the form of at least one current stress level.

The data analysis is used particularly for detecting an alteration in the at least one stress level, i.e. establishing whether the at least one current stress level has increased or decreased in comparison with a previous stress level. The user is therefore provided with a tool for obtaining information particularly about changes in his at least one current stress level in comparison with earlier stress levels over time and, following autonomous rating of the detected changes, if need be taking individual measures for stress reduction.

In order to ascertain a current stress level for a user, the evaluation unit can resort to biometric data pertaining to the user that have been ascertained in the past, for example, and can take said biometric data into account when ascertaining said current stress level. Thus, biometric data pertaining to the user that have been ascertained in the past can be used as reference data in order to perform user-specific calibration. The current stress level is ascertained in relation to the available reference data.

Similarly, the evaluation unit can resort to not only the biometric data from the user but also to biometric data from other users when ascertaining a current stress level. By way of example, this allows clusters of user groups to be formed, for example according to age, sex or profession. To ascertain the current stress level for a user, the data from other users in the same user group can be taken into account.

In one preferred embodiment, the evaluation unit ascertains a current stress level for a user using artificial neural networks. The artificial neural networks are trained on the basis of the available biometric data from a multiplicity of users. As a result of the training, the artificial neural network learns progressively as well and can thereby further improve the quality of the ascertained current stress level.

By way of example, the artificial neural network can be realized on the basis of a multilayer perceptron network. This neural network consists of a plurality of layers, a permanent input layer and a permanent output layer and if need be further intermediate layers, with no feedback taking place from one layer to layers situated before it.

The artificial neural network can consist of precisely three layers, for example, input layer, hidden layer and output layer. In this case, the seven categories of biometric data, for example, sleep, speech, motor functions, social interaction, economic data, personal data and questionnaire data, can form the neurons of the input layer. In another embodiment, a relatively large number of neurons are used in the input layer by virtue of more finely granular category features being used as neurons of the input layer. In another embodiment, the artificial neural network has feedback mechanisms. When the artificial neural network has feedback mechanisms, it is transited multiple times (iteratively).

In a further-developed embodiment, the evaluation unit ascertains a current stress level for a user using a network of artificial neural networks, for example using a Deep Belief Network. The network of artificial neural networks is made up of a plurality of neural networks that interact with one another. In a network of neural networks, a single neural network comprises an input layer and a hidden layer. A first level of neural networks is provided. In the neural networks on the first level, the input layer is stipulated by the biometric data from the user. By way of example, the input layer of a first-level neural network can be stipulated by the biometric data from the user in precisely one category. From the input layer of an artificial neural network, it is possible to determine the hidden layer of the same neural network. Furthermore, a second and possibly further level of neural networks is provided. For a neural network on the second and every further level, the input layer can be determined using the hidden layers of a plurality of neural networks on the preceding level. The current stress level can be determined from at least one neural network on a topmost level.

The multiplicity of biometric data parameters, which particularly includes a combination of different categories of biometric data that are used for ascertaining the at least one current stress level, means that the apparatus disclosed in this application and also the disclosed method and the disclosed application allow very much more reliable ascertainment of the at least one current stress level than is afforded by the known apparatuses and methods mentioned at the outset that ascertain a current stress level only on the basis of a single or very few biometric data parameter(s) in the same category.

Furthermore, the quality of the analysis of the biometric data is increased further by the neural network method used, since, as time progresses and the database available for training the neural network becomes larger, said method can make ever more precise statements and hence further improves the reliability of the method for determining a current stress level.

As the cited instances of application show, the further application can determine a plurality of biometric data pertaining to the user that belong to different categories solely from the user-specific use data from available applications on the mobile terminal, on the one hand, and from signal data, on the other hand, which are produced by sensors integrated in the mobile terminal. Hence, the apparatus according to the invention and the method according to the invention and the application according to the invention provide a user with an inexpensive and non-time-consuming solution for determining a current stress level. Furthermore, the solution according to the invention dispenses with additional apparatuses, particularly sensors, that the user needs to fix or wear directly on his body. The solution does not restrict the user in any way in terms of comfort, wellbeing or look, as is entailed by the application or wearing of specific apparatuses with sensors.

The at least one current stress level determined by the evaluation unit can either be made accessible to the user via the Internet or can be made accessible to the user on the mobile terminal, for example by sending an SMS to the user. The analysis data consisting of the at least one current stress level and possibly further evaluation data, for example statistics pertaining to the change in a stress level over time, can alternatively be transmitted to the mobile terminal using the same transmission paths as when transmitting biometric data from the mobile terminal to the central server, but in the opposite direction. To this end, a transmission unit for transmitting data from the server to the mobile terminal is provided on the central server. Similarly, a reception unit for receiving data from the central server is provided on the mobile terminal. The analysis data can also be transmitted from the central server to the mobile terminal using a push service. The data transmission is in turn effected in encrypted form.

Further details and advantages of the invention will become clear from the description below of exemplary embodiments with reference to the figures, in which:

FIG. 1 shows a schematic illustration of the apparatus for ascertaining a current stress level;

FIG. 2 shows a schematic illustration of the further application for ascertaining a current stress level;

FIG. 3a shows a flowchart for a first instance of application, sleep;

FIG. 3b shows a flowchart for a second instance of application, motor functions;

FIG. 3c shows a flowchart for a third instance of application, speech;

FIG. 5a shows a schematic illustration of an exemplary embodiment of the evaluation unit;

FIG. 5b shows a schematic illustration of an alternative exemplary embodiment of the evaluation unit;

FIG. 5c shows a schematic illustration of a further alternative exemplary embodiment of the evaluation unit;

FIG. 6 shows a schematic illustration of an exemplary embodiment of the evaluation unit with a plurality of artificial neural networks.

DESCRIPTION OF EXEMPLARY EMBODIMENTS OF THE INVENTION

Figure 4A:
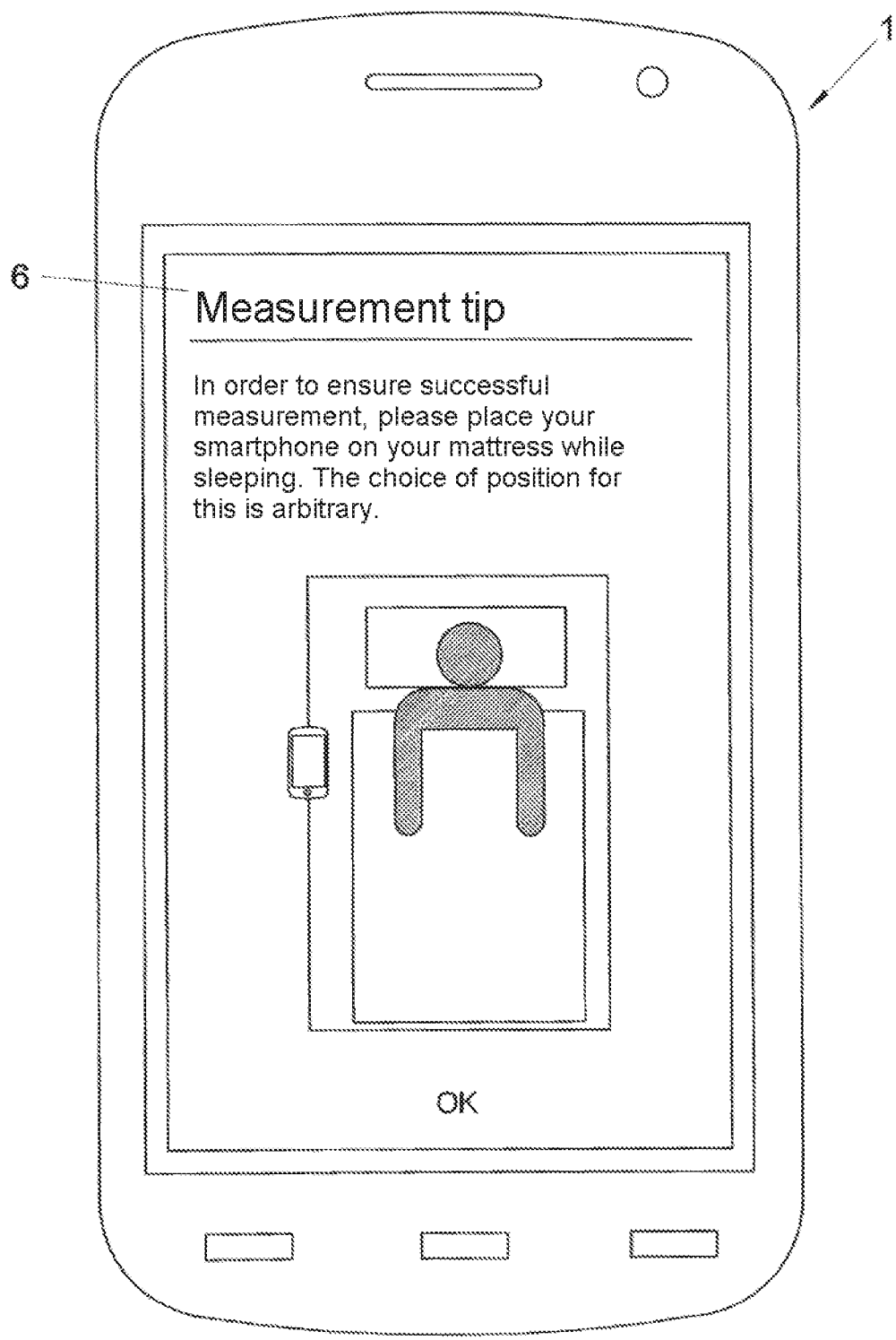
FIG. 4a shows a graphical user interface for starting the sleep instance of application.

FIG. 1 shows a schematic illustration of an embodiment of the apparatus for ascertaining a current stress level 36, 36A, 36B, 36C, 36D. The apparatus comprises a mobile terminal 1 and a central server 10.

The mobile terminal 1 contains a plurality of sensors 2, for example a gyroscope 21, an acceleration sensor 22, a light sensor 23 and/or a microphone 24. The signal data 31 produced by the sensors 2 can be accessed via an operating system 4. The operating system 4 is executed within an execution unit 3 and manages the access to the hardware components of the mobile terminal 1, for example the sensors 2. In addition, different applications, for example a plurality of available applications 5 and a further application 6, are executed in the execution unit 3.

The further application 6 ascertains a plurality of biometric data 33 pertaining to a user of the mobile terminal 1. By way of example, the further application 6 is implemented in the programming language Java. The further application 6 uses the MVC (model view controller) design pattern as a basic design pattern. The use of the MVC design pattern structures the further application 6 such that this facilitates the comprehensibility and also the extendability and adjustability of the further application 6 to new and/or altered hardware components and operating systems 4.

The further application 6 obtains the biometric data 33 from signal data 31 that are produced by the sensors 2 and that can be accessed by means of the operating system 4. The access to the signal data 31 is realized by the further application 6, for example through the use of the observer design pattern. The observer design pattern provides the further application 6 with simplified and standardized access to the signal data 31.

The further application 6 can extract a plurality of further biometric data 33 from the use data 32 from available applications 5 too. The use data 32 produced by the available applications 5 are accessible via the operating system 4. The access to the use data 32 is realized by the further application 6, for example through the use of the observer design pattern. The observer design pattern provides the further application 6 with simplified and standardized access to the use data 32. An observer is informed about status changes on the object that it is observing, for example an available application 5. If the available application 5 is an SMS application, for example, and the user calls the SMS application in order to write a new SMS, then the observer observing the SMS application is informed about this status change. The further application 6 reacts to the writing of a new SMS that is observed by the observer by recording the characters input by the user, for example using a keypad, providing them with a timestamp and storing them in the local memory unit 7 as use data 32 for the SMS application.

By way of example, it is also possible for all keypad inputs by the user to be recorded regardless of their use in a specific application. To this end, an observer or a plurality of observers is implemented for the sensor keypad 25, for example one observer for each key on the keypad. As soon as a key on the keypad is pressed by the user, the observer observing the key is informed of said pressing of a key. The further application 6 reacts to the pressing of the key that is observed by this observer by virtue of the further application 6 checking whether the user has pressed a delete key or another key. The 'delete key' or 'other key' information is recorded by the further application 6, provided with a timestamp, and these data are stored in the local memory unit 7 as signal data 31.

From the stored signal data 31 and/or use data 32, the further application 6 extracts a plurality of biometric data 33. The biometric data 33 are subdivided into categories, for example into the categories sleep, speech, motor functions, social interaction, economic data, personal data and questionnaire data. For each category, a category-specific ascertainment time interval is defined, for example 30 seconds for the sleep category and 20 milliseconds for the speech category. The signal data 31 and/or use data 32 that are relevant to a category are processed in a first pre-processing step using category-specific time intervals to produce conditioned signal data 31A and/or conditioned use data 32A. In order to determine the data that are relevant to a capture time interval, the timestamps stored for the signal data 31 and/or use data 32 are evaluated. The conditioned signal data 31A and/or conditioned use data 32A are in turn provided with a timestamp. In a second processing step, the biometric data 33 are extracted from a sequence of conditioned signal data 31A and/or conditioned use data 32A. By way of example, for an instance of application, for example the writing of an SMS, biometric data 33 in the motor functions category are ascertained from the conditioned use data 32A pertaining to the SMS written. The biometric data 33 pertaining to a category that are ascertained in an instance of application are also referred to as a feature vector for this category. For each feature vector, a timestamp is determined that stipulates the time interval for which the feature vector is valid. The biometric data 33 comprise the feature vectors ascertained for the various categories, with the respective timestamps of said feature vectors. The biometric data 33 ascertained by the further application 6 are stored in a local memory unit 7 of the mobile terminal 1.

Furthermore, the mobile terminal 1 has a transmission unit 8A and a reception unit 8B. The transmission unit 8A transmits data 34 from the mobile terminal 1 to an external node, for example the central server 10. The transmission is effected via the air interface, for example. The reception unit 8B receives data from an external node, for example the central server 10. The transmission unit 8A is used to transmit data 34, for example the biometric data 33 from the user, to the central server 10 for the purpose of evaluation. The reception unit 8B is used to receive data 34 coming from the central server 10, for example evaluations 35 created by the central server. Each evaluation 35 is provided with a timestamp that stipulates the time interval for which the evaluation is valid. An evaluation 35, for example a current stress level 36, 36A, 36B, 36C, 36D of a user of the mobile terminal 1, is transferred to the further application 6 for display and displays to the user on the display 9 of the mobile terminal 1 by means of the operating system 4.

The central server 10 has a transmission unit 18A and a reception unit 18B. The reception unit 18B is used to receive data 34 from another node, for example the mobile terminal 1. By way of example, the received data 34 are biometric data 33 from the user of the mobile terminal 1. The received data 34 are stored in a central memory unit 17. Furthermore, an evaluation unit 13 is provided on the central server 10. The evaluation unit 13 evaluates the received biometric data 33. By way of example, the evaluation unit 13 determines the at least one current stress level 36, 36A, 36B, 36C, 36D at an instant t by evaluating those feature vectors for the received biometric data 33 whose timestamps are valid at the instant t.

The current stress level 36A determines a first current stress level of the user for a first category of biometric data 33, for example the sleep category. The current stress level 36C determines a second current stress level of the user for a second category of biometric data 33, for example the motor functions category. The current stress level 36B determines a third current stress level of the user for a third category of biometric data 33, for example the speech category. The current stress level 36D determines a fourth current stress level of the user for a fourth category of biometric data 33, for example the social interaction category, or for a combination of categories of biometric data, for example the social interaction, economic data, personal data and/or questionnaire data categories. In addition, further current stress levels can be determined for further categories and/or combinations of categories. The current stress level 36 determines a consolidated current stress level of the user that is obtained from a combination of the category-specific stress levels 36A, 36B, 36C, 36D and if need be of available further category-specific stress levels, for example by forming the arithmetic mean of the category-specific stress levels.

The at least one evaluation 35 determined by the evaluation unit 13, for example the at least one current stress level 36, 36A, 36B, 36C, 36D, comprises, for each evaluation 35, a timestamp that stipulates the time interval for which the evaluation 35 is valid. The at least one evaluation 35, for example the at least one current stress level 36, 36A, 36B, 36C, 36D is stored in the central memory unit 17 and transmitted to the mobile terminal 1 via the transmission unit 18A.

FIG. 2 shows a schematic illustration of an embodiment of the further application 6 for ascertaining at least one current stress level 36, 36A, 36B, 36C, 36D. The further application 6 comprises a plurality of components, for example a data manager 61, a data preprocessor 62 and a data analyzer 63.

The signal data 31 and/or use data 32 made available via the operating system 4 are loaded into the data manager 61 and managed thereby. The data manager 61 transfers the signal data 31 and/or use data 32 to the data preprocessor 62. The data preprocessor 62 conditions the signal data 31 and/or use data 32 and transfers the conditioned signal data 31A and/or conditioned use data 32A back to the data manager 61. The data manager 61 stores the conditioned signal data 31A and/or conditioned use data 32A in the local memory unit 7. The data manager 61 transfers the conditioned signal data 31A and/or conditioned use data 32A to the data analyzer 63. The data analyzer 63 analyzes the conditioned signal data 31A and/or conditioned use data 32A and determines the biometric data 33 therefrom.

For those biometric data 33 that are evaluated locally, the data analyzer 63 creates at least one evaluation 35, for example in the form of at least one current stress level 36, 36A, 36B, 360, 36D. The data analyzer 63 transfers the biometric data 33 and if need be the at least one evaluation 35 to the data manager 61. Insofar as at least one evaluation 35 has been created by the data analyzer 63, the data manager 61 visualizes the at least one evaluation 35 for the user of the mobile terminal 1 by displaying it on the display 9. The data manager 61 transfers the biometric data 33 to the transmission unit 8A for transmission to the central server 10, insofar as the biometric data 33 are evaluated centrally.

That evaluation 35 that is provided in the form of the consolidated current stress level 36 can be visualized on the display 9 continuously, for example, as a traffic light icon. The traffic light icon can display the colors green, amber or red on the basis of the consolidated current stress level 36. If the consolidated current stress level 36 is normalized to an integer value in the value range [0,10], for example, then the traffic light color is chosen on the basis of the current value of the consolidated current stress level 36. A high value corresponds to a high consolidated current stress level 36. A low value corresponds to a low consolidated current stress level 36. If the consolidated current stress level 36 is low, for example in the value range [0,3], the color green is displayed. If the consolidated current stress level 36 is increased, for example in the value range [4,6], the color amber is displayed. If the consolidated current stress level 36 of the user is high, for example in the value range [7,10], the color red is displayed. The display of the consolidated current stress level 36 is updated as soon as a consolidated current stress level 36 is available with a timestamp that is more recent than the timestamp of the previously displayed consolidated stress level.

In a further embodiment, the consolidated current stress level 36 is visualized as a bar chart having 10 bars. Each bar in the bar chart has an associated integer value from the value range [0,10], to which the consolidated current stress level 36 is normalized.

If biometric data 33 have been transferred to the central server 10 for the purpose of evaluation, the data manager 61 receives at least one evaluation 35, for example in the form of a third current stress level 36B for the speech category, pertaining to the biometric data 33 for the speech category that are evaluated on the server.

When the data manager 61 receives a new evaluation 35, for example in the form of a third current stress level 36B for the speech category, it ascertains a new consolidated current stress level 36 from the category-specific current stress levels, known to the data manager 61, whose timestamps are currently still valid. By way of example, the consolidated current stress level 36 is obtained by means of the arithmetic mean or by means of a weighted mean of the category-specific current stress levels 36A, 36B, 36C, 36D that are still valid. The data manager 61 visualizes the consolidated current stress level 36 on the display 9, for example by updating the traffic light icon.

The consolidated current stress level 36 of the user is an individual variable. By way of example, when the further application 6 is first used by a user, user-specific calibration can be performed. To this end, the user is asked to record biometric data 33 in the personal data category, for example via a form integrated in the further application 6. On the basis of the personal data, an individual current stress level of the user is determined, which stipulates a calibration factor, for example. The individual current stress level, for example in its manifestation as a calibration factor, is taken into account for determining the current stress level 36, 36A, 36B, 36C, 36D for the user.

FIG. 3A shows a flowchart for a first instance of application, sleep. The first instance of application, sleep, ascertains biometric data 33 in the sleep category for the purpose of ascertaining a first current stress level 36A of a user. The first instance of application describes a first method for ascertaining said first current stress level 36A. Prior to first use of the sleep instance of application, the user allows the mobile terminal 1 to fall onto his mattress from a height of approximately 30 centimeters. By evaluating the sensor data 2, the further application 6 computes the spring temper and the damping constant of the mattress, which are stored as calibration data pertaining to the sleep instance of application. The sleep instance of application ascertains motion data during the rest phase of the user and evaluates said data.

(A1): the sleep instance of application requires direct user interaction.

(A2): In this regard, the user of the mobile terminal 1 calls the sleep mode of the further application 6. In one possible embodiment, calling the sleep mode automatically prompts the mobile terminal 1 to be put into flight mode in order to minimize emissions of electromagnetic radiation by the mobile terminal 1. The user positions the mobile terminal 1 on the mattress during his rest phase.

(A3): The signal data 31 produced by the sensors 2, for example the gyroscope 21, the acceleration sensor 22 and the light sensor 23 during the rest phase are collected by the further application 6 and stored in the local memory unit 7.

(A4): Following termination of the rest phase, the user deactivates the sleep mode in the further application 6. If need be, this also deactivates the flight mode and hence activates the transmission unit 8A and the reception unit 8B.

(A5): The data manager 61 of the further application 6 loads the sensor data ascertained during the sleep mode in the further application 6 and transfers these signal data 31 to the data preprocessor 62.

(A6): The data preprocessor 62 divides the ascertained signal data 31 into time intervals, for example into time intervals having a length of 30 seconds. For the signal data 31 in each time interval, conditioned signal data 31A that are characteristic of the time interval are determined and are provided with a timestamp.

(A7): The data preprocessor 62 transfers the conditioned signal data 31A with their timestamps to the data manager 61.

(A8): The data manager 61 stores the conditioned signal data 31A with their timestamps in the local memory unit 7.

(A9): The data manager 61 transfers the conditioned signal data 31A with their timestamps to the data analyzer 63 for the purpose of evaluation.

(A10): The data analyzer 63 analyzes the conditioned signal data 31A and determines therefrom a feature vector with biometric data 31 in the sleep category. By way of example, the feature vector is determined by means of a statistical regression model for modeling a binary target variable, for example a logit or probit model. To this end, the sequence of conditioned signal data 31A that is obtained by arranging the conditioned signal data 31A according to ascending timestamps is evaluated and each element in the sequence is classified as "awake" or "asleep" for the sleep state. The classification takes account of the sleep states of the preceding elements in the sequence, that is to say the sleep states in the preceding time intervals. If the probability of the user being in a sleep state in a time interval is greater than 50%, the time interval is classified with the state "asleep", otherwise with the state "awake". The sequence of sleep states over all time intervals is given as a basis for determining the feature vector.

By way of example, the feature vector of the biometric data 33 pertaining to the sleep category comprises the following features:
   a. Sleep onset latency
   b. Sleep efficiency
   c. Sleep onset instant
   d. Sleep end
   e. Time in bed
   f. Sleep duration
   g. Wakeful time h. Length of time to the first REM phase
i. Stage components of the individual sleep phases
j. Number of awakenings
k. Number of sleep stage changes From the feature vector of the biometric data 33 pertaining to the sleep category, the data analyzer 63 determines an evaluation 35 that comprises particularly the first current stress level 36A for the sleep category. In order to ascertain the first current stress level 36A, all features of the feature vector are rated with an integer value for the value range [0,10], for example, and the individual values are used to form a mean value, for example an arithmetic mean or a weighted mean. In addition, the rating is influenced to some extent by the user-specific calibration, for example as a result of a calibration factor that needs to be taken into account. By way of example the first current stress level 36A for the sleep category is obtained as an integer value in the value range [0,10]. The first current stress level 36A comprises a timestamp that stipulates the period for which the first current stress level 36A for the sleep category is valid.

(A11): The feature vector of the biometric data 33 pertaining to the sleep category and also the evaluation 35, which particularly comprises the first current stress level 36A for the sleep category, are transferred to the data manager 61.

(A12): The data manager 61 stores the feature vector of the biometric data 33 pertaining to the sleep category and also the evaluation 35, particularly the first current stress level 36A for the sleep category, in the local memory unit 7. The data manager 61 visualizes the evaluation 35, particularly the first current stress level 36A for the sleep category, on the display 9. From the first current stress level 36A for the sleep category and if need be further available, valid current stress levels for further categories, for example the current stress levels 36B, 36C, 36D, the data manager 61 determines a consolidated current stress level 36 and visualizes the consolidated current stress level 36, for example by updating the traffic light icon.

FIG. 4A shows an exemplary graphical user interface for the start of the sleep instance of application of the further application 6. The exemplary graphical user interface contains a tip for successful measurement of the biometric data 33 pertaining to the sleep category. By selecting the OK button, the user can start the instance of application.

Figure 4B:
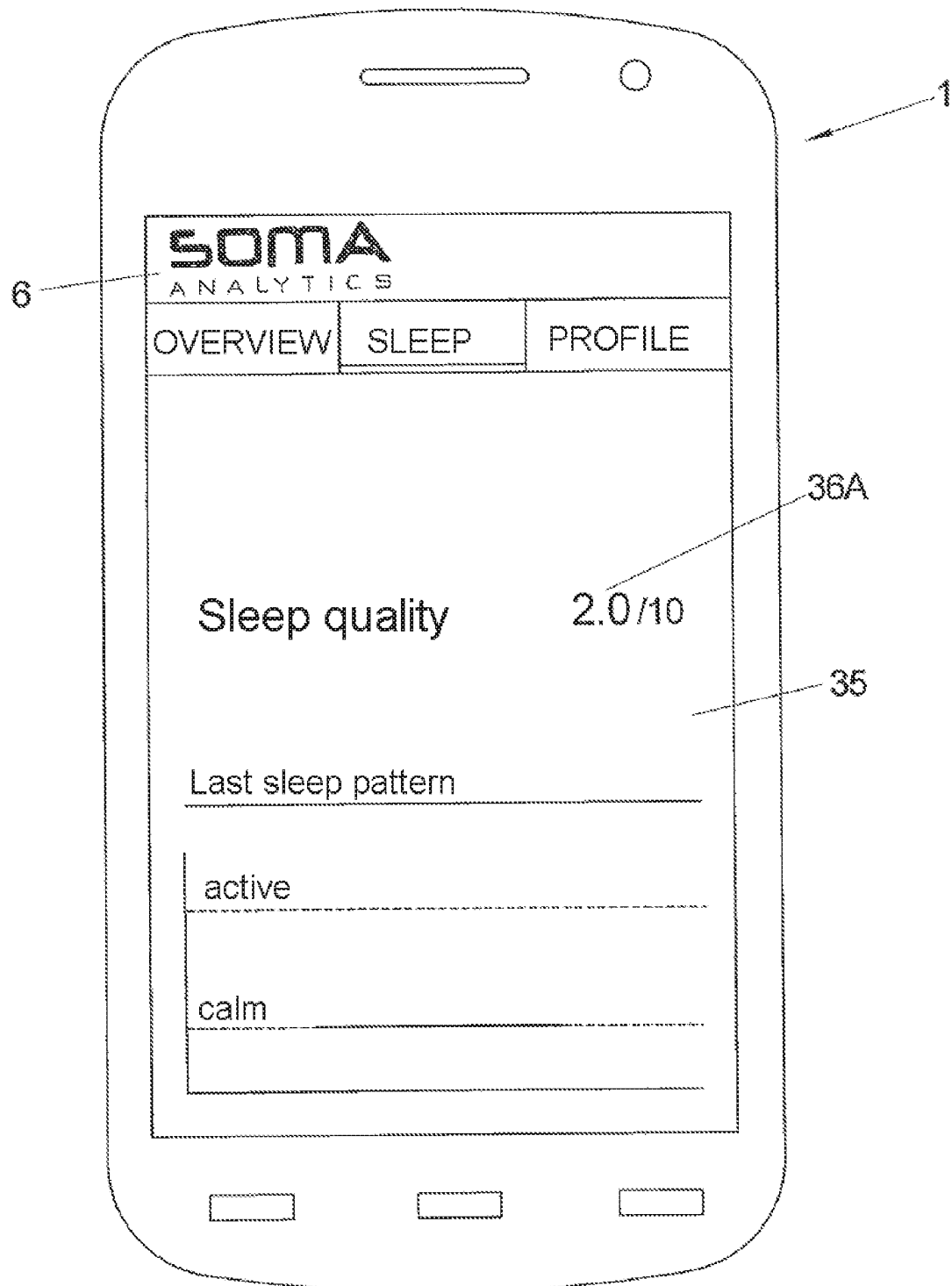
FIG. 4b shows a further graphical user interface for a first evaluation display.

FIG. 4B shows a further exemplary graphical user interface of a first evaluation display for the sleep instance of application. The first evaluation display visualizes an evaluation 35 for the sleep category in the form of an overview evaluation. The sleep quality parameter is used to display a first current stress level 36A of the user for the sleep category. The sleep quality is indicated by the numerical value 2.0 within a scale from 0 to 10. In addition, the first evaluation display comprises further elements, for example the last sleep pattern as a function of time.

Figure 4C:
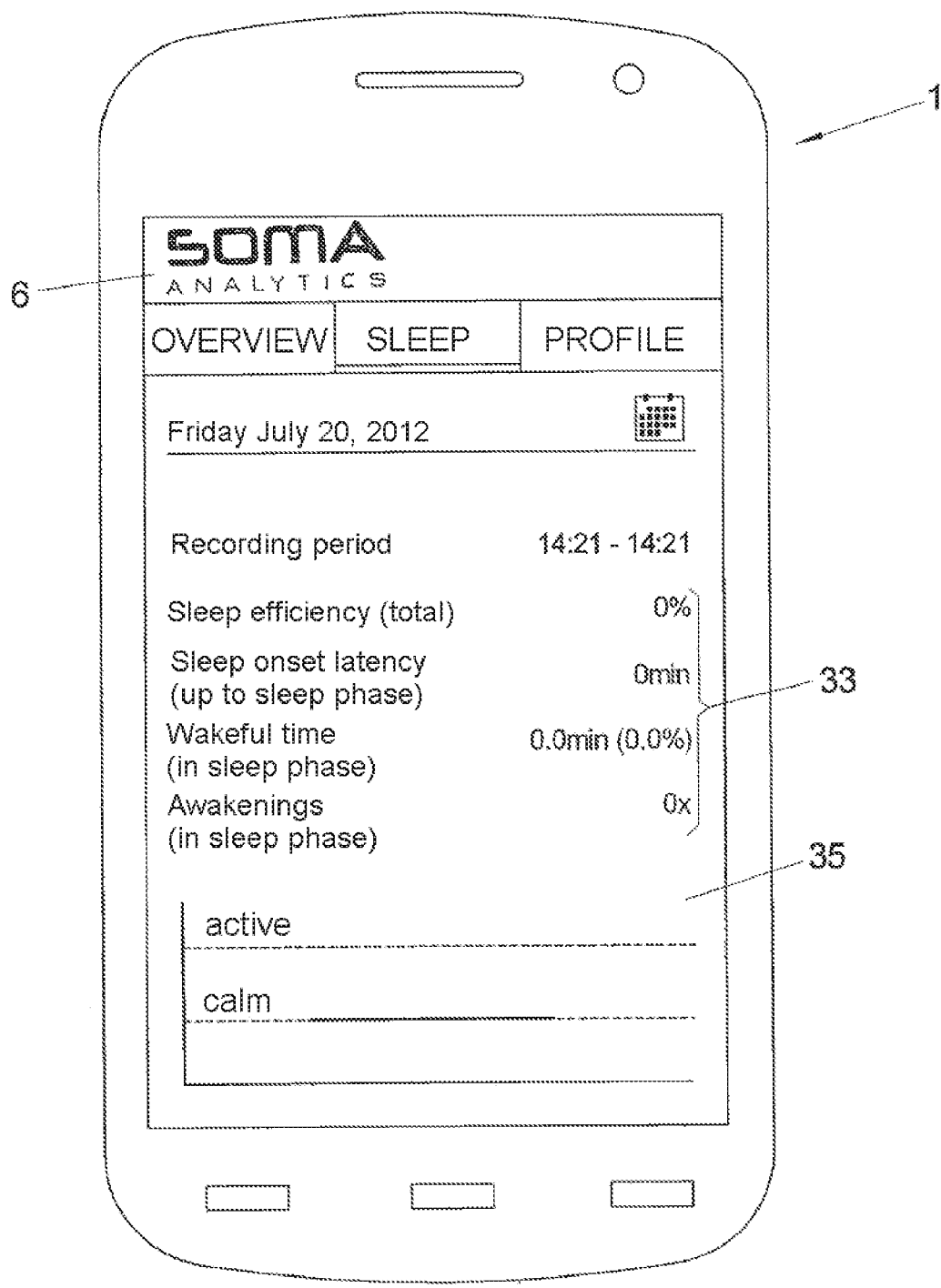
FIG. 4c shows a further graphical user interface for a second evaluation display.

FIG. 4C shows a further exemplary graphical user interface of a second evaluation display for the sleep instance of application. The second evaluation display visualizes an evaluation 35 for the sleep category in the form of a detail display. The detail display comprises the ascertained biometric data 33 pertaining to the sleep category. For each feature of the biometric data 33 in the sleep category, the ascertained value is indicated.

Figure 4D:
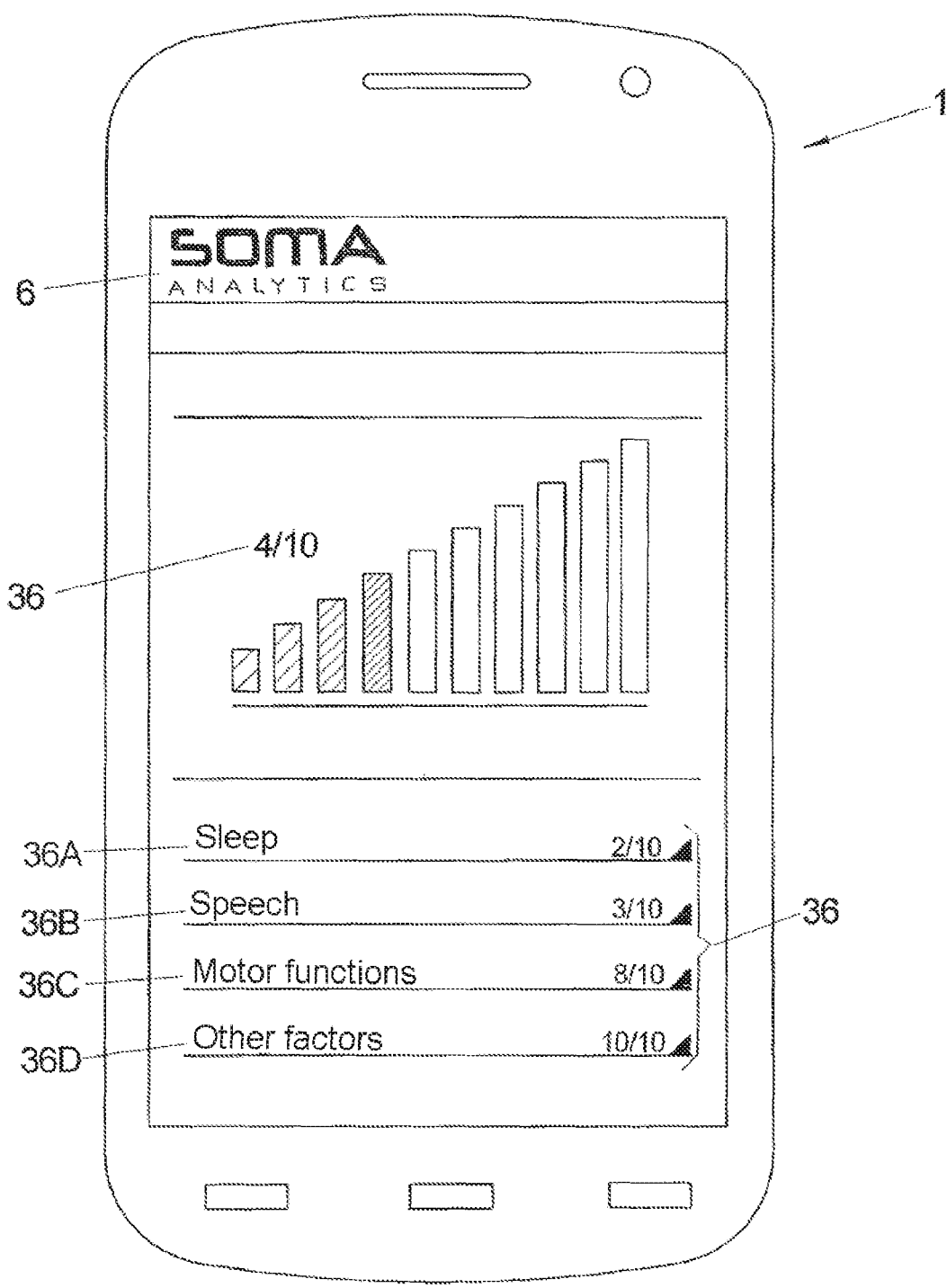
FIG. 4d shows a further graphical user interface for a third evaluation display.

FIG. 4D shows a further graphical user interface of a third evaluation display for the sleep instance of application. The third evaluation display visualizes the consolidated current stress level 36 in a bar chart. In addition, the consolidated stress level 36 and the current stress levels 36A, 36B, 36C, 36D for the individual categories are displayed as numerical values. Each numerical value is displayed in a color that is specific to the value. The choice of color visualizes the current stress levels 36, 36A, 36B, 36C, 36D in color.

FIG. 3B shows a flowchart for a second instance of application, motor functions. The second instance of application, motor functions, ascertains biometric data 33 in a motor functions category for the purpose of ascertaining a second current stress level 36C of a user. The second instance of application describes a second method for ascertaining the second current stress level 360. This instance of application requires only indirect interaction with the user.

(B1): The further application 6 has been loaded into the execution unit 3 of the mobile terminal 1 and has been started. The further application 6 runs in the execution unit 3 as a background process.

(B2): The user calls an available application 5 that is associated with a text input via the keypad, for example an SMS application for writing a new SMS.

(B3): The user uses the keypad 25 of the mobile terminal 1 to type an SMS, for example.

(B4): The sequence of keypad inputs that is made by the user is collected by the data manager 61 of the further application 6 and stored on the local memory unit 7. For each keypad input, a timestamp is stored.

(B5): The user terminates typing, for example by finishing and sending the SMS.

(B6): The data manager 61 transfers the collected and stored keypad data to the data preprocessor 62.

(B7): The data preprocessor 62 performs pre-evaluation of the keypad data. To this end, the data preprocessor 62 divides the ascertained keypad data into time intervals, for example into time intervals with a length of 15 seconds. For the keypad data 32 in each time interval, conditioned use data 32A that are characteristic of the time interval are determined and are provided with a timestamp.

(B8): The conditioned use data 32A provided with timestamps are transferred from the data preprocessor 62 to the data manager 61.

(B9): The data manager 61 stores the conditioned use data 32A provided with timestamps in the local memory unit 7.

(B10): The data manager 61 transfers the conditioned use data 32A provided with timestamps to the data analyzer 63.

(B11): The data analyzer 63 analyzes the conditioned use data 32A provided with timestamps and determines a feature vector therefrom with biometric data 31 in the motor functions category.

By way of example, the data analyzer 63 determines the error rate from the frequency of keypad input errors, particularly from the number of times the user operates a delete key in the time interval under consideration. The error rate determined is a measure of the hand/eye coordination of the user.

By way of example, the feature vector of the biometric data pertaining to the motor functions category comprises the following features:
a. Speed (keystrokes per unit time)
b. Error rate
c. Variance in the error rate
d. Variance in the speed From the feature vector of the biometric data 33 pertaining to the motor functions category, the data analyzer 63 determines an evaluation 35, particularly the second current stress level 36C for the motor functions category. To this end, all features of the feature vector are rated with an integer value from the value range [0,10], for example, and a mean value, for example an arithmetic mean or a weighted mean, is formed from the individual values. In addition, the rating is influenced to some extent by the user-specific calibration, for example as a result of a calibration factor that needs to be taken into account. The second current stress level 36C for the sleep category is obtained as an integer value in the value range [0,10] for example. The second current stress level 36C comprises a timestamp that stipulates the period for which the second current stress level 36C for the sleep category is valid.

(B12): The data analyzer 63 transfers the feature vector of the biometric data 33 pertaining to the sleep category and also the evaluation 35, particularly the second current stress level 36C for the motor functions category, with its timestamp, to the data manager 61.

(B13): The data manager 61 stores the feature vector of the biometric data 33 pertaining to the sleep category and also the evaluation 35, particularly the second current stress level 36C for the motor functions category, with its timestamp, in the local memory unit 7. The data manager 61 visualizes the evaluation 35, particularly the second current stress level 36C for the motor functions category, on the display 9. From the second current stress level 36C for the motor functions category and if need be further available valid current stress levels for further categories, the data manager 61 determines the consolidated current stress level 36 and visualizes it, for example by updating the traffic light icon.

In an alternative embodiment, the biometric data 31, for example the biometric data 31 pertaining to the sleep and/or motor functions categories, are transmitted to the central server 10, stored in the central memory unit 17 and evaluated by the evaluation unit 13 arranged on the server.

FIG. 3C shows a flowchart for a third instance of application, speech. The third instance of application, speech, ascertains biometric data 33 in the speech category, for example the speech parameters speech rate and/or modulation capability, in order to ascertain a third current stress level 36B of a user. The third instance of application describes a third method for ascertaining the third current stress level 36B. This instance of application requires only indirect interaction with the user.

The speech instance of application comprises voice analysis of voice data from the user, for example voice data from telephone calls conducted by the user using the mobile terminal 1.

(C1): The further application 6 has been loaded into the execution unit 3 of the mobile terminal 1 and has been started. The further application 6 runs as a background process in the execution unit 3.

(C2): The speech instance of application is started by an incoming call to the mobile terminal 1, for example.

(C3): The user takes the call.

(C4): During the call, the data manager 61 of the further application 6 continuously collects the voice data 31 pertaining to the user that are captured via the microphone 24, provides them with a timestamp and stores voice data 31 with the timestamp in the local memory unit 7.

(C5): The user terminates the call.

(C6): The data manager 61 transfers the voice data 31 stored with a timestamp to the data preprocessor 62.

(C7): The data preprocessor 62 performs pre-evaluation of the voice data 31. To this end, the data preprocessor 62 divides the captured voice data 31 into time intervals, for example into time intervals with a length of 20 milliseconds. For the voice data 31 in each time interval, conditioned voice data 31A that are characteristic of the time interval are determined and are provided with a timestamp.

(C8): The data preprocessor 62 transfers the conditioned voice data 31A with their timestamps to the data manager 61.

(C9): The data manager 61 stores the conditioned voice data 31A for heir timestamps in the local memory unit 7.

(C10): The data manager 61 transfers the conditioned voice data 31A with their timestamps to the data analyzer 63 for the purpose of evaluation.

(C11): The data analyzer 63 analyzes the conditioned voice data 31A and determines from them a feature vector with biometric data 31 in the speech category.

By way of example, the feature vector of the biometric data 31 for the speech category comprises the following features:
 a. Accent shape
 b. Average pitch
 c. Contour slope
 d. Final Lowering
 e. Pitch range
 f. Speech rate
 g. Stress frequency
 h. Breathiness
 i. Brilliance
 j. Loudness
 k. Pause Discontinuity
 l. Pitch Discontinuity
 m. Time in different emotional states (state 1, state n)

The feature vector is provided with a timestamp and these data are transferred from the data analyzer 63 to the data manager 61 as biometric data 33 in the speech category.

(C12): The data manager 61 stores the feature vector provided with a timestamp in the local memory unit 7 as biometric data 33 in the speech category. The data manager 61 transfers the biometric data 33 pertaining to the speech category to the transmission unit 8A for the purpose of transmission to the central server 10.

(C13): The reception unit 18B of the central server 10 receives the transmitted data in the form of the biometric data 33 pertaining to the speech category. The central server 10 stores the biometric data 33 in the central memory unit 17 and evaluates the biometric data 33 in the evaluation unit 13. To this end, a neural network method—explained further on—is used, for example. The evaluation unit 13 determines an evaluation 35. The evaluation 35 particularly comprises the third current stress level 36B in the speech category. The third current stress level 36B for the speech category is determined as an integer value in the value range [0,10], for example. The third current stress level 36B comprises a timestamp that stipulates the period for which the third current stress level 36B for the speech category is valid.

(O14): The central server 10 transmits the evaluation 35, particularly the third current stress level 36B for the speech category, with its timestamp, to the mobile terminal 1 by means of the transmission unit 18A. The transmitted evaluation 35 is received by the reception unit 8B of the mobile terminal 1 and transferred to the data manager 61 of the further application 6.

(C15): The data manager 61 stores the evaluation 35, particularly the third current stress level 36B for the speech category, with its timestamp, in the local memory unit 7. The data manager visualizes the evaluation 35, particularly the third current stress level 36B for the speech category, on the display 9. From the third current stress level 36B for the speech category and if need be further available, valid current stress levels for further categories, the data manager 61 determines the consolidated current stress level 36 and visualizes the consolidated current stress level 36, for example by updating the traffic light icon.

Besides the cited sleep, speech and motor functions instances of application, there are further instances of application that ascertain further biometric data 33 for further categories and determine further current stress levels of the user therefrom.

Thus, the social interaction instance of application evaluates use data 32 from the user from such available applications 5 as are used for social interaction. Examples of available applications 5 that are used for social interaction are SMS applications, e-mail applications or social network applications, such as an instant messaging application or a Facebook application. From the use data 32 pertaining to the available applications 5 that are used for social interaction, it is possible to ascertain, by way of example, the number of contacts in social networks or the frequency with which contact is made, for example the frequency with which an SMS is sent.

By way of example, the feature vector of the biometric data 33 pertaining to the social interaction category comprises the following features:
 a. Number of telephone contacts
 b. Number of contacts in social networks
 c. Frequency with which contact is made (SMS, telephoning, messages in the social network)
 d. Length of time for which contact is made
 e. Time at which contact is made
 f. Frequency at which contact is made
 g. Absolute and relative number of contacts with regular contact being made In addition, biometric data 33 in further categories can be taken into account, for example biometric data 33 in the economic data category, in the personal data category and/or in the questionnaire data category.

The economic data category relates to comprehensive rather than user-specific data, for example data pertaining to general sickness absence rate or pertaining to job security.

By way of example, the feature vector of the biometric data 33 pertaining to the economic data category comprises the following features:
 a. Sickness absence rate
 b. Job risk The personal data category comprises data pertaining to age and family status and also pertaining to occupation group and pertaining to education level. The feature vector of the personal data category is used particularly for individual calibration of the current stress levels 36, 36A, 36B, 360, 36D. The personal data are recorded by the user using a form within the further application 6, for example.

By way of example, the feature vector of the biometric data 33 pertaining to the personal data category comprises the following features:
 a. Occupation group
 b. Educational level
 c. Geoposition
 d. Age
 e. Medication
 f. Pre-existing illnesses
 g. Family illnesses
 h. Family status The questionnaire data comprise individual self-assessments by the user pertaining to stress-related questions. The questionnaire data are recorded by the user using a form within the further application 6, for example.

The biometric data 33 pertaining to the cited further categories can additionally be used for evaluation and particularly for ascertaining the consolidated current stress level 36 of the user.

Whereas, in the exemplary sleep and motor functions instances of application, the biometric data 33 are evaluated by the further application 6 directly as an evaluation unit on the mobile terminal 1, a different approach has been chosen for the exemplary speech instance of application. In order to increase the quality of the ascertained third current stress level 36B and also of the consolidated current stress level 36, the evaluation of the biometric data 33 pertaining to the speech category is effected in the evaluation unit 13 that is arranged on the central server 10. The evaluation unit 13 contains an evaluation method, for example a method based on artificial neural networks that resorts to biometric data 33 from other users and to earlier biometric data 33 from the user.

In an alternative embodiment of the invention, the biometric data 33 from other categories are also evaluated in the evaluation unit 13 arranged on the central server 10 in order to increase the quality of the evaluation further.

In another alternative embodiment of the invention, the evaluation method obtained on the central server 10 by training the artificial neural network method is implemented in the further application 6, for example by means of an update in the further application 6. In this case, the evaluation unit is provided for all categories by the further application 6 on the mobile terminal 1. Evaluation of the biometric data 33 pertaining to all categories is effected on the mobile terminal 1 rather than on the central server 10.

FIG. 5A shows a schematic illustration of an exemplary embodiment of the evaluation unit 13 on the central server 10. In this embodiment, a current stress level 36, 36A, 36B, 36C, 36D is determined for a user by the evaluation unit 13 on the central server 10.

In a variation of this embodiment, it is alternatively possible for a portion of the biometric data 33 pertaining to the user to be analyzed and evaluated on the mobile terminal 1 directly and for at least one current stress level 36A, 36B, 36C, 36D ascertained on the terminal to be determined. A second portion of the biometric data 33 pertaining to the user is analyzed and evaluated on the central server 10 by the evaluation unit 13 and at least one current stress level 36A, 36B, 36C, 36D on the server is determined. The biometric data 33 analyzed and evaluated on the server can comprise biometric data 33 that are also taken into account for the analysis and evaluation on the mobile terminal 1. A consolidated stress level 36 that takes account both of the at least one current stress level 36A, 36B, 36C, 36D ascertained on the terminal and of the at least one current stress level 36A, 36B, 36C, 36D ascertained on the server is determined by the data manager 61 of the further application 6.

The evaluation unit 13 comprises a server-end data manager 14 and a server-end data analyzer 15. The server-end data analyzer 15 is in the form of an artificial neural network 40 in the form of a multilayer perceptron network. The neural network consists of three layers: the input layer 43, the hidden layer 44 and the output layer 45. Each layer is constructed from neurons 46. The input layer 43 contains a plurality of input neurons 46A. The hidden layer 44 contains a plurality of hidden neurons 46B and the output layer 45 contains precisely one output neuron 46C.

In one possible embodiment, each input neuron 46A of the input layer 43 has, as an associated input value, the value of a feature from a feature vector in a category of biometric data 33 that have been transmitted to the central server 10, for example in the speech category, following suitable normalization, for example to the value range [0,10].

In one alternative embodiment, each input neuron 46A of the input layer 43 has, as an associated input value, the current stress level for a category of biometric data 33. By way of example, the input layer 43 consists of seven input neurons 46A, each input neuron 46A having the associated current stress level of one of the categories sleep, speech, motor functions, social interaction, economic data, personal data and questionnaire data.

In a further alternative embodiment, the features of the category-specific feature vectors, of biometric data 33 available to the central server 10, are linked and evaluated in another way in order to determine the input values of the input neurons 46A.

The multilayer perceptron network is in the form of a feed forward network, i.e. the connections between the neurons 46 always point from one layer, for example the input layer 43, to the next layer, for example the hidden layer 44. When the neural network 40 is transited, no feedback or cyclic connections occur, and instead information is forwarded only in one distinguished direction. The input neurons 46A of the input layer have connections to the hidden neurons 46B of the hidden layer. By way of example, each input neuron 46A of the input layer can have one connection to each hidden neuron 46B of the hidden layer. In an initial state, the hidden layer 44 has a greater number of neurons 46 than the input layer 43. By contrast, the output layer 45 contains precisely one neuron 46, the output neuron 46C. The neurons 46B of the hidden layer 44 have connections to the output neuron 46O of the output layer 45. By way of example, each hidden neuron 46B of the hidden layer 44 is connected to the output neuron 46C. The output neuron 46C represents a current stress level 36, 36A, 36B, 36C, 36D of a user.

From the biometric data 33 from a user, the artificial neural network 40 computes a current stress level 36, 36A, 36B, 36C, 36D of the user. For this purpose, the server-end data manager 14 retrieves the biometric data 33 pertaining to a user in the form of the feature vectors for the ascertained categories—transmitted to the central server 10—of biometric data 33 from the central memory unit 17. The feature vectors suitable for computing the current stress level 36, 36A, 36B, 36C, 36D are taken into account, for example the feature vectors with the most recent timestamp. A feature vector in a category is taken into account only if the instant for which the current stress level 36, 36A, 36B, 36C, 36D is computed lies in the validity range defined by the timestamp. The server-end data manager 14 provides the biometric data 33 for the data analyzer 15, which is in the form of an artificial neural network 40.

Following possible conditioning, such as normalization and/or suitable linking, the biometric data 33 are read into the input layer 43 of the neural network 40 and forwarded to the next layers of the neural network 40 via the connections. Each connection has a connection weight that has either a boosting or inhibiting effect. Each neuron 46B of the hidden layer 44 has an activation function, for example the hyperbolic tangent activation function, which maps an arbitrary input value onto the value range [−1, 1]. The input value for a neuron 46B of the hidden layer 44 is obtained as a sum of the values transmitted via the weighted connections. For each neuron 46, a neuron-specific threshold value is stipulated. If, following application of the activation function, the input value exceeds the threshold value of the neuron 46B, this computed value is forwarded from the hidden neuron 46B to its outgoing connections and hence to the output neuron 46C in the output layer 45. The output neuron 46C determines its output value using the same method as has been described for a hidden neuron 46B of the hidden layer 44. For given connection weights, activation functions and threshold values, the artificial neural network 40 determines the value of the one output neuron 46C in a deterministic fashion from the biometric data 33 that are associated with the input neurons 46A. The value of the output neuron 46C provides the current stress level 36, 36A, 36B, 36C, 36D.

The value of the output neuron 46C is transferred from the server-end data analyzer 15 in the form of an artificial neural network 40 to the server-end data manager 14. The server-end data manager 14 stores the output value as a current stress level 36, 36A, 36B, 36C, 36D for the categories relevant to determination thereof, with a timestamp, in the central memory unit 17.

In an initial phase, the connection weights of each connection and the threshold values of each neuron 46 are stipulated. By way of example, the connection weight for a connection is stipulated by a random value from the range [−0.5, 0.5], the value 0 being omitted. The threshold value for a neuron 46 is stipulated by a random value from the range [−0.5, 0.5] for example.

In a training phase, the connection weights of each connection of the neural network 40 and the threshold values for each neuron 46 are adjusted. For the purpose of training the neural network 40, a monitored learning method, preferably a back propagation method, is used. In the case of a monitored learning method, the desired output value from the output neuron 46C is available for the input values for the neural network 40. By way of example, the desired output value from the output neuron 46C is obtained from the current stress level for the questionnaire data category, which level has been ascertained exclusively from the questionnaire data answered by the user. In an iterative back propagation method, the connection weights of all connections and the threshold values of all neurons 46 are trained until the output value that the neural network 40 provides for the output neuron 46C matches the desired output value with sufficient accuracy. The repeated with a multiplicity of biometric data 33 from a multiplicity of users allows the analysis and evaluation method provided by the artificial neural network 40 for ascertaining the current stress level 36, 36A, 36B, 36C, 36D to be constantly improved and adjusted further.

FIG. 5B shows a schematic illustration of an alternative exemplary embodiment of the evaluation unit 13 on the central server 10. In this alternative embodiment, the artificial neural network 40 is in the form of a feedback neural network. Besides the connections that point from a neuron 46 of an upstream layer to a neuron 46 of a downstream layer, for example from an input neuron 46A of the input layer 43 to a hidden neuron 46B of the hidden layer 44, this embodiment has connections that run in the opposite direction, for example from a hidden neuron 46B of the hidden layer 44 to an input neuron 46A of the input layer 43 or from the output neuron 46C of the output layer 45 to a hidden neuron 46B of the hidden layer 44. An artificial neural network 40 of this kind has a higher level of complexity than the previously described feed forward network, which forwards data only in a distinguished forward direction.

A development of the feedback artificial neural network is shown in FIG. 5C. Accordingly, lateral feedback loops are also possible, that is to say connections of neurons 46 that are arranged in the same layer. In a further development of the feedback artificial neural network, there is also provision for direct feedback. Direct feedback is a connection from a neuron 46 to itself. Direct feedback means that neurons 46 inhibit or boost themselves in order to arrive at their activation limits.

A feedback artificial neural network is provided particularly in order to take account of the "memory" of biometric data 33 pertaining to a user when determining the current stress level 36, 36A, 36B, 36C, 36D. The memory of biometric data 33 pertaining to a category pertaining to a user is the sequence, arranged on the basis of their timestamp, of feature vectors for this category and this user; in particular, the sequence comprises older feature vectors from earlier analyses. A suitable subsequence is selected and the artificial neural network method is started with the first feature vector in this subsequence, that is to say the feature vector with the oldest timestamp. In a first time step, the values of the first feature vector are applied to the artificial neural network as input values and the neural network is transited once. The built-in feedback loops mean that the values from the first time step have a further effect on the subsequent time step. In the subsequent time step, the values of the second feature vector are applied to the artificial neural network 40 as input values. When the artificial neural network 40 is transited again, in addition to the input values for the second feature vector the values generated in feedback connections from the previous time step are taken into account as new input values. The method determined in this manner is continued further until the complete subsequence of feature vectors has been transited. The value of the output neuron 46C provides the current stress level 36, 36A, 36B, 36C, 36D of the user.

FIG. 6 shows a schematic illustration of an embodiment of the invention that has been developed further. In this embodiment, the evaluation unit 6, 13 ascertains a current stress level 36, 36A, 36B, 36C, 36D of a user using a network of artificial neural networks. By way of example, the network of neural networks may be in the form of a deep belief network or a convolutional deep belief network 50.

A single artificial neural network 40, which is part of the network of artificial neural networks, may be embodied according to one of the embodiments cited previously for artificial neural networks 40, for example.

In a preferred embodiment the network of artificial neural networks comprises a plurality of artificial neural networks 40 that interact with one another. By way of example, the plurality of artificial neural networks 40 may be embodied as a restricted Boltzmann machine or as a convolutional restricted Boltzmann machine.

In the network of artificial neural networks 40, a single neural network 40 comprises an input layer 43 and a hidden layer 44. The input layer comprises a plurality of input neurons 46A. The hidden layer comprises a plurality of hidden neurons 46B. From the input layer of an artificial neural network, it is possible to determine the hidden layer of the same neural network, as explained in the preceding embodiments, for example.

The network of artificial neural networks contains a first level of artificial neural networks 40, which are referred to as first neural networks. The input layer 43 of the first neural networks is stipulated by the biometric data 33 from the user. By way of example, a component of a feature vector in a category can be associated with an input neuron 46A. Furthermore, at least one further level of artificial neural networks 40 is provided, which are referred to as further neural networks. For a further neural network, the input layer 43 can be determined from the hidden layers 44 of a plurality of artificial neural networks 40 on the preceding level. By way of example, an input neuron 46A of the input layer 43 is stipulated by precisely one hidden neuron 46B of an artificial neural network 40 from the preceding layer. Alternatively, an input neuron 46A of the input layer 43 is stipulated by a plurality of hidden neurons 46B of one or more artificial neural networks 40 from the preceding layer.

The network of artificial neural networks 40 contains a topmost level that comprises at least one artificial neural network 40. The at least one artificial neural network 40 on the topmost level is referred to as the topmost neural network.

The at least one topmost neural network has an output layer 45. In a first embodiment, the hidden layer 44 of a topmost neural network is identified by means of the output layer 45. In a second embodiment, the at least one artificial neural network 40 of the topmost level comprises three layers, the input layer, the hidden layer and the output layer 45. In the second embodiment, the output layer 45 comprises precisely one output neuron 46C.

The current stress level 36, 36A, 36B, 36C, 36D can be determined from the output layer 45 of the at least one topmost neural network. In a first embodiment, a classifier is provided that classifies the output layer 45 and determines the current stress level 36, 36A, 36B, 36C, 36D therefrom. By way of example, the classifier may be designed as a support vector machine. In a second embodiment, the current stress level 36, 36A, 36B, 36C, 36D is stipulated by the output neuron 46C.

The evaluation unit 6, which comprises a network of a plurality of artificial neural networks 40, is designed such that the computation of the network can be parallelized. The evaluation unit 6, 13 interacts with at least one processor, the processor being designed and provided to compute neurons 46, 46B, 46C for at least one artificial neural network 40. By way of example, the processor may be arranged on the mobile terminal 1. The processor may also be provided on a central server. In a preferred embodiment, a plurality of processors are provided. The plurality of processors may be provided on the mobile terminal or the central server or on both. The evaluation unit 6, 13 is designed and provided to have the plurality of artificial neural networks 40 computed by the plurality of processors in parallel.

The parallel computation optimizes the computation time. The method for determining a current stress level that is based on a network of artificial neural networks can be executed more quickly by parallelizing the computation of neural networks. Similarly, the parallelization allows power to be saved.

In a further development, at least one graphics card with at least one graphics card processor can be incorporated for executing the method, the at least one graphics card being arranged on the mobile terminal or on the central server. The graphics card processor can support computation of the artificial neural networks, in particular. This approach allows the computation time to be optimized even further.

We claim:
1. A device for calculating a current load level of a user, comprising:
    a mobile end unit having:
        at least one signal data generating sensor integrated into the mobile end unit,
        a plurality of available applications for use by the user, and
        an evaluation unit provided in the mobile end unit or in a central server, wherein:
the mobile end unit has a further application designed for calculating biometric data about the user, at least from the at least one signal data produced by said at least one sensor, and from user data of said plurality of available applications used by the user, and making the biometric data available to the evaluation unit,
wherein the biometric data from the at least one signal data produced by said at least one sensor, and user data of said plurality of available applications, is divided into a plurality of categories,
wherein category-specific load levels are ascertained by the evaluation unit by means of an arithmetic mean or a weighted mean of features relating to the biometric data pertaining to each category in the plurality of categories,
the evaluation unit is designed for determining the current load level of the user from the biometric data by applying a method carried out in a network of artificial neural networks that includes a plurality of artificial neural networks that interact with each other,
a plurality of processors are arranged on the mobile end unit or on the central server, which are designed for calculating the plurality of artificial neural networks in parallel, and
at least one graphics card with at least one graphics card processor is arranged on the mobile end unit or on the central server and the at least one graphics card processor supports the calculation of the artificial neural networks, and
wherein the determined current load level of the user is displayed to the user via the mobile end unit in the form of a consolidated load level obtained from a combination of category-specific load levels by the evaluation unit forming the arithmetic mean or weighted mean of the category-specific load levels.

2. The device according to claim 1, wherein the evaluation unit is designed for determining the current load level of the user from the biometric data by using a method that is carried out on the plurality of artificial neural networks, which are designed as a Convolutional Deep Belief Network.

3. The device according to claim 1, wherein the further application can be stored as a Subscriber Identification Module (SIM) application in the memory area on a SIM card that can be operated in the mobile end unit and can be executed by a separate execution unit integrated on the SIM card.

4. The device according to claim 3, wherein the evaluation unit is designed for determining the current load level of the user from the biometric data by using a method that is carried out on the plurality of artificial neural networks, which are designed as a Convolutional Deep Belief Network.

5. The device according to claim 1, wherein the biometric data can be divided into a plurality of categories, wherein the categories relate to one or more of:
sleep,
speech,
motor skills,
social interaction,
economic data,
personal information, and
questionnaire data.

6. The device according to claim 1, wherein:
each artificial neural network includes two neuron layers, one input layer and one hidden layer,
the input layer includes a plurality of input neurons
the hidden layer includes a plurality of hidden neurons, and
wherein the input neurons can be determined by the biometric data.

7. The device according to claim 6, wherein the evaluation unit is designed for determining the current load level from at least one output neuron, which is identifiable with at least one hidden neuron of at least one artificial neural network.

8. The device according to claim 6, wherein:
the evaluation unit is designed for determining the input layer of at least one of the artificial neural networks through the hidden layers of a plurality of other artificial neural networks.

9. The device according to claim 8, wherein the evaluation unit is designed for determining the current load level from at least one output neuron, which is identifiable with at least one hidden neuron of at least one artificial neural network of the plurality of artificial neural networks.

10. The device according to claim 6, wherein the evaluation unit cooperates with the plurality of processors and the respective processor is designed for calculating neurons for at least one of the plurality of artificial neural networks.

11. The device according to claim 1, wherein the at least one sensor integrated into the mobile end unit comprises at least one of:
a gyroscope,
an acceleration sensor, and
a light sensor.

12. A method for calculating a current load level of a user of a mobile end unit, comprising:
starting a further application installed on the mobile end unit so that this is carried out on the mobile end unit,
calculating biometric data of the user by means of the further application, wherein the biometric data is recorded at least from user data that is recorded from using a plurality of applications present and available on the mobile end unit by the user, and calculated from at least one signal data produced by at least one sensor integrated into the mobile end unit,
wherein the biometric data from the at least one signal data is produced by said at least one sensor, and user data of said plurality of available applications, is divided into a plurality of categories,
evaluating the biometric data with an evaluation unit provided in the mobile end unit or in a central server for determining the current load level,
wherein:
category-specific load levels are ascertained by means of an arithmetic mean or a weighted mean of features relating to the biometric data pertaining to each category in the plurality of categories,
the evaluation unit determines the current load level with the aid of a network of artificial neural networks,
the network of artificial neural networks comprises a plurality of artificial neural networks that interact with each other,
the plurality of artificial neural networks calculates in parallel with a plurality of processors,
the plurality of processors is arranged on the mobile end unit or on the central server,
at least one graphics card processor of at least one graphics card supports the calculation of the artificial neural networks, wherein the at least one graphics card with the at least one graphics card processor is arranged on the mobile end unit or on the central server, and wherein the determined current load level of the user is displayed to the user via the mobile end unit in the form of a consolidated load level obtained from a combination of category-specific load levels by forming the arithmetic mean or weighted mean of the category-specific load levels.

13. The method according to claim 12, wherein the evaluation unit trains each artificial neural network on the basis of biometric data and from load levels evaluated for the biometric data determined, which improves the quality of the artificial neural network.

14. The method according to claim 12, wherein:

the further application, as long as it is carried out on the mobile end unit, verifies that signal data is provided at least by the at least one sensor integrated into the mobile end unit, or that usage data is provided by the at least one application available on the mobile end unit for calculating the biometric data, the further application calculates the biometric data at least from the provided signal data or the provided usage data during a successful verification and equips this with a time stamp, and the evaluation unit determines the current load level from the biometric data, the time stamp of which is currently valid.

15. The method according to claim 14, wherein the evaluation unit trains each artificial neural network on the basis of biometric data and from load levels evaluated for the biometric data determined, which improves the quality of the artificial neural network.

16. A non-transitory computer-operable medium that stores computer-executable code associated with an application for a mobile end unit, wherein the computer-executable code, when executed, causes at least one processor of the end unit to carry out the method according to claim 12.

17. The device according to claim 1, wherein for each category, a category-specific ascertainment time interval is defined, and the signal data and use data that are relevant to a category are processed using category-specific time intervals to produce conditioned signal data and conditioned use data.

18. The method according to claim 12, wherein for each category, a category-specific ascertainment time interval is defined, and the signal data and use data that are relevant to a category are processed using category-specific time intervals to produce conditioned signal data and conditioned use data.

* * * * *

(12) EX PARTE REEXAMINATION CERTIFICATE (12781st)
United States Patent
Schneider et al.

(10) Number: US 11,468,984 C1
(45) Certificate Issued: Dec. 3, 2024

(54) DEVICE, METHOD AND APPLICATION FOR ESTABLISHING A CURRENT LOAD LEVEL

(71) Applicant: SOMA ANALYTICS UG (HAFTUNGSBESCHRÄNKT), Munich (DE)

(72) Inventors: Peter Schneider, Dresden (DE); Johann Huber, Bruckmühl (DE); Christopher Lorenz, Munich (DE); Diego Alberto Martin-Serrano Fernandez, London (GB)

(73) Assignee: MOBILE HEALTH INNOVATIVE SOLUTIONS, LLC, Cheyenne, WY (US)

Reexamination Request:
No. 90/019,549, Jun. 25, 2024

Reexamination Certificate for:
Patent No.: 11,468,984
Issued: Oct. 11, 2022
Appl. No.: 16/850,984
Filed: Apr. 16, 2020

Related U.S. Application Data

(63) Continuation of application No. 14/418,374, filed as application No. PCT/EP2013/066241 on Aug. 1, 2013, now abandoned.

(51) Int. Cl.
*A61B 5/00* (2006.01)
*A61B 5/11* (2006.01)
*A61B 5/16* (2006.01)
*G06N 3/04* (2023.01)
*G06N 3/045* (2023.01)
*G06N 3/08* (2023.01)
*G06N 3/084* (2023.01)
*G06N 3/088* (2023.01)
*G10L 25/63* (2013.01)
*G10L 25/66* (2013.01)
(Continued)

(52) U.S. Cl.
CPC ............ *G16H 40/67* (2018.01); *A61B 5/165* (2013.01); *A61B 5/4803* (2013.01); *A61B 5/4809* (2013.01); *A61B 5/4812* (2013.01); *A61B 5/4815* (2013.01); *A61B 5/4884* (2013.01); *A61B 5/7267* (2013.01); *G06N 3/04* (2013.01); *G06N 3/045* (2023.01); *G06N 3/084* (2013.01); *G06N 3/088* (2013.01); *G10L 25/63* (2013.01); *G10L 25/66* (2013.01); *G16B 40/20* (2019.02); *G16H 50/20* (2018.01); *A61B 5/1124* (2013.01); *A61B 5/4806* (2013.01); *A61B 5/486* (2013.01); *A61B 5/6898* (2013.01); *A61B 5/7264* (2013.01); *G06N 3/044* (2023.01); *G16B 40/00* (2019.02)

(58) Field of Classification Search
None
See application file for complete search history.

(56) References Cited

To view the complete listing of prior art documents cited during the proceeding for Reexamination Control Number 90/019,549, please refer to the USPTO's Patent Electronic System.

*Primary Examiner* — Robert L Nasser

(57) ABSTRACT

The invention relates to a device, a method, a computer program product and an application for establishing a current load level of a user. The device and the method comprise a mobile terminal, which comprises at least one sensor generating signal data and a plurality of available applications for use by the user and also an evaluation unit. According to the invention, provision is made for the mobile terminal to comprise an application, which is configured as further application and establishes a plurality of biometric data in respect of the user, at least from the signal data or from available applications used by the user, and to make said data available to the evaluation unit, and for the evaluation unit to determine the current load level of the user from the biometric data.

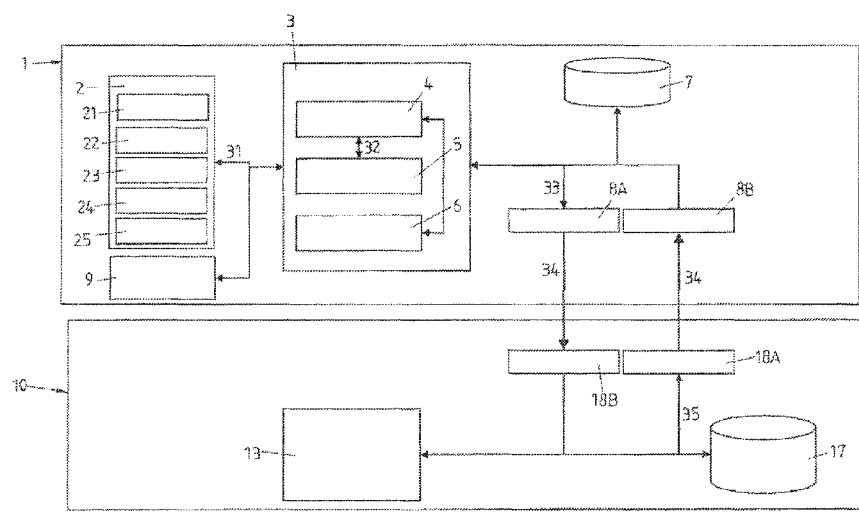

(51) Int. Cl.
*G16B 40/00* (2019.01)
*G16B 40/20* (2019.01)
*G16H 40/67* (2018.01)
*G16H 50/20* (2018.01)
*G06N 3/044* (2023.01)

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1, 5, 11, 12, 13 and 16 is confirmed.

Claims 2-4, 6-10, 14, 15, 17 and 18 were not reexamined.

\* \* \* \* \*